(12) United States Patent
Strobel et al.

(10) Patent No.: US 9,624,515 B2
(45) Date of Patent: Apr. 18, 2017

(54) SYSTEM AND METHOD OF PRODUCING VOLATILE ORGANIC COMPOUNDS FROM FUNGI

(71) Applicants: Gary A. Strobel, Bozeman, MT (US); Angela R. Tomsheck, Oilmont, MT (US)

(72) Inventors: Gary A. Strobel, Bozeman, MT (US); Angela R. Tomsheck, Oilmont, MT (US)

(*) Notice: Subject to any disclaimer, the term of this patent is extended or adjusted under 35 U.S.C. 154(b) by 78 days.

(21) Appl. No.: 13/757,325

(22) Filed: Feb. 1, 2013

(65) Prior Publication Data
US 2013/0137131 A1 May 30, 2013

Related U.S. Application Data

(63) Continuation-in-part of application No. 13/110,688, filed on May 18, 2011, now Pat. No. 8,501,458.

(60) Provisional application No. 61/593,671, filed on Feb. 1, 2012, provisional application No. 61/345,918, filed on May 18, 2010.

(51) Int. Cl.
| | |
|---|---|
| *A01N 1/02* | (2006.01) |
| *C12P 17/18* | (2006.01) |
| *C12P 5/00* | (2006.01) |
| *C12P 7/26* | (2006.01) |
| *C12P 17/06* | (2006.01) |
| *C12R 1/645* | (2006.01) |
| *C12N 15/01* | (2006.01) |

(52) U.S. Cl.
CPC ............ *C12P 17/181* (2013.01); *C12N 15/01* (2013.01); *C12P 5/002* (2013.01); *C12P 7/26* (2013.01); *C12P 17/06* (2013.01); *C12R 1/645* (2013.01)

(58) Field of Classification Search
None
See application file for complete search history.

(56) References Cited

U.S. PATENT DOCUMENTS

| | | | |
|---|---|---|---|
| 4,275,234 A | 6/1981 | Baniel et al. | |
| 4,297,109 A | 10/1981 | Sugito et al. | |
| 5,348,872 A | 9/1994 | Lin et al. | |
| 5,510,526 A | 4/1996 | Baniel et al. | |
| 5,641,406 A | 6/1997 | Sarhaddar et al. | |
| 5,831,122 A | 11/1998 | Eyal | |
| 2003/0186425 A1 | 10/2003 | Strobel et al. | |
| 2005/0220769 A1 | 10/2005 | Strobel et al. | |
| 2009/0123977 A1* | 5/2009 | Mendez et al. | 435/91.4 |
| 2010/0272690 A1 | 10/2010 | Gandhi et al. | |
| 2010/0285543 A1* | 11/2010 | Strobel et al. | 435/126 |
| 2011/0287471 A1 | 11/2011 | Strobel et al. | |
| 2013/0252289 A1 | 9/2013 | Strobel et al. | |

FOREIGN PATENT DOCUMENTS

| | | |
|---|---|---|
| CN | 102071144 | 5/2011 |
| WO | WO 93/00440 | 1/1993 |
| WO | 2012/159161 | 11/2012 |

OTHER PUBLICATIONS

Azra et al. Microbiology (2004) 150. 4023-4031.*
Sanchez-Ballesteros et al (Mycologia, 92(5): 967-977 (2000) Abstract only.*
Hsieh et al. (Mycologia, 97(4):844-865 (2005).*
Azeez, S. (2008). "Fennel. In Chemistry of Spices", pp. 227-241. Edited by Parthasarathy, V.A., Chempakam, B., & Zachariah, T. Cambridge, MA: CAB International.
Barton, A., & Tjandra, J. (1989). "Eucalyptus oil as a cosolvent in water-ethanol-gasoline mixtures." Fuel 68, 11-17.
Bunge, M., et al. (2008). "On-line monitoring of microbial volatile metabolites by proton transfer reaction-mass spectrometry." Appl Environ Microbiol 74, 2179-2186.
Cook, et al. (2007). "Mentha spicata essential oils rich in 1,8.cineole and 1,2-epoxy-P-methane derivates from Zakynthos (Ionian Island, W Greece)". The Journal of Essential Oil Research 19, 225-230.
Cosimi, et al., (2009). "Bioactivity and qualitative analysis of some essential oils from Mediterranean plants against stored-product pests: Evaluation of repellency against Sitophilus zeamais Matschulsky, Cryptolestes ferrugineus (Stephens) and Tenebrio molitor (L.)." Journal of Stored Products Research 45, 125-132.
Croteau, et al., (1994). "Biosynthesis of monoterpenes: partial purification, characterization and mechanism of action of 1,8-cineole synthase." Arch-Biochem-Biophys 309, 184-192.
Ezra, et al., (2004a). "New endophytic isolates of *Muscodor albus*, a volatile-antibiotic-producing fungus." Microbiology 150, 4023-4031.
Ezra, et al., (2004b). Proton transfer reaction-mass spectroscopy as a technique to measure volatile emissions of Muscodor albus. Plant Science 166, 1471-1477.
Kempler, G.M. (1983). "Production of Flavor Compounds by Microorganisms. III. Terpenenes." B. Production of Monoterpenes by Microorganisms. In Advances in Applied Microbiology, vol. 29, pp. 35-37. Edited by A.I. Laskin. New York, NY: Academic Press, Inc.
Madyastha, K. M. (1984). "Microbial transformations of acyclic monoterpenes." Journal of Chemical Sciences 93, 677-686.
Smith, S.A., et al. (2008) "Bioactive Endophytes Warrant Intensified Exploration and Conservation" PloS 1 Biology Published on-line Aug. 25, 2008. PloS 1 3(8):e3052.

(Continued)

*Primary Examiner* — J. Hines
*Assistant Examiner* — Khatol Shahnan Shah
(74) *Attorney, Agent, or Firm* — Riverside Law LLP

(57) ABSTRACT

An isolated fungus is described. The isolated fungus produces at least one compound selected from the group consisting of 1,8-cineole, 1-methyl-1, 4-cyclohexadiene, and (+)-α-methylene-α-fenchocamphorone. A method for producing at least one compound selected from the group consisting of 1,8-cineole, 1-methyl-1, 4-cyclohexadiene, and (+)-α-methylene-α-fenchocamphorone is also described. The method includes culturing a fungus on or within a culturing media in a container under conditions sufficient for producing the at least one compound.

9 Claims, 8 Drawing Sheets

(56) References Cited

OTHER PUBLICATIONS

Southwell, et al., (2003), "Melaleuca teretifolia chemovars: New Australian sources of citral and 1,8-cineole." Journal of Essential Oil Research 15:339-341.
Strobel, G.A., & Daisy, B. (2003). "Bioprospecting for Microbial Endophytes and Their Natural Products." Microbiology and Molecular Biology Reviews 67, 491-502.
Strobel, et al., (2001). "Volatile antimicrobials from *Muscodor albus*, a novel endophytic fungus." Microbiology 147, 2943-2950.
Strobel, et al., (2008). "The production of myco-diesel hydrocarbons and their derivatives by the endophytic fungus *Gliocladium roseum* (NRRL 50072)." Microbiology 154, 3319-3328.
Tan, R., & Zou, W. (2001). "Endophytes: a rich source of functional metabolites." Nat. Prod. Rep. 18, 448-459.
Thomas, et al., (2000). "Plant sources of aroma chemicals and medicines in India." Chemical Industry Digest (Special Millennium Issue), 104-108.
Weyerstahl, et al., (1993). "Constituents of the Leaf Essential Oil of *Persea indica* (L.) K. Spreng." Flavour and Fragrance Journal 8, 201-207.
Worapong, et al., (2001). "*Muscodor albus* anam. nov., an endophyte from Cinnamomun zeylanicum." Mycotaxon 79, 67-79.
Griffin et al., (1989) "Protoplast formation and transformation of Hypoxylon mammatum." Abstracts of the 1989 APS Annual Meeting. Phytopathology 79:1135; p. 1204.
Zhao et al., (2004) "Study on the Preparation and Regeneration of Protoplast From Taxol-Producing Fungus *Nodulisporium ylviforme*." Nature and Science 2(2):52-59.
Johannesson (2000) Ecology of *Daldinia* spp. With Special Emphasis on *Daldinia zoculata*. Doctoral thesis. Swedish University of Agricultural Sciences Uppsala.
Srutka et al., (2007) "Daldinia decipiens and Entonaema cinnabarina as fungal symbionts of Xiphydria wood wasps." Mycological Research 111:224-231.
Gu et al., (2007) "Cytotoxic benzo[j]fluoranthene metabolites from Hypoxylon truncatum IFB-18, an endophyte of Artemisia annua." J. Nat. Prod. 70:114-117.
Rapparini et al., (2008) "Effect of arbuscular mycorrhizal (AM) colonization on terpene emission and content of Artemisia annua L." Plant Biology 10:108-122.
Shwab et al., (2007) "Histone Deacetylase Activity Regulates Chemical Diversity in *Aspergillus*." Eukaryotic Cell 6:1656-1664.
Williams et al., (2008) "Epigenetic remodeling of the fungal secondary metabolome." Organic & Biomolecular Chemistry 6:1895-1897.
Brosch et al., (2008) "Histone modifications and chromatin dynamics: a focus on filamentous fungi." FEMS Microbiol. Rev. 32:409-439.
Bok et al. (2009) "Chromatin-level regulation of biosynthetic gene clusters." Nature Chemical Biology.
Mooibroek et al. (1990) "Introduction of hygromycin B resistance into *Schizophyllum commune*: Preferential methylation of donor DNA." Molecular and General Genetics 222:41-48.
Birch et al. (1998) "A reporter system for analysis of regulatable promoter functions in the basidiomycete fungus *Phanerochaete chrysosporium*." Journal of Applied Microbiology 85:417-424.
Cheng et al. (2003) "Inhibition of DNA Methylation and Reactivation of Silenced Genes by Zebularine." Journal of the National Cancer Institute 95:399-409.
Cichewicz (2009) "Epigenome manipulation as a pathway to new natural product scaffolds and their congeners." Natural Product Reports 27:11-22.
Tomsheck et al. (2010) *Hypoxylon* sp., an Endophyte of Persea indica, Producing 1,8-Cineole and Other Bioactive Volatiles with Fuel Potential. Microbial Ecology 60:903-914.
Quang et al. Cohaerins C-F, "Four Azaphilones from the Xylariaceous fungus *Annulohypoxylon cohaerens*." Tetrahedron. 2006, 62, pp. 6349-6354.
Sanchez-Ballesteros et al., "Phylogenetic Study of *Hypoxylon* and related genera based on ribosomal ITS sequences", Mycologia, 97(4): 844-865, 2005. Abstract only.
Hsieh et al. "Molecular Phylogeny of *Hypoxylon* and Closely related genera," Mycologia, 97(4): 844-865 (2005).
Kamenarska et al. "Botanica Marina". vol. 52, Issue 1 (Feb. 2009). Abstract only.
Extended European Search Report dated Dec. 3, 2013 for European Patent Application No. 11 784 182.5, 7 Pages.
Japanese Notice of Rejection and English translation dated Jul. 22, 2015 for Japanese Patent Application No. 2013-511337, 24 Pages.
Russian Office Action and English translation dated May 20, 2015 for Russian Patent Application No. 2012154695, 9 pages.
Mexican Office Action and English translation dated Aug. 6, 2015 for Mexican Patent Application No. MX/a/2012/013448, 19 pages.
First Chinese Office Action and English translation dated Jun. 27, 2014 for Chinese Patent Application No. 201180035508X, 35 pages.
Second Chinese Office Action and English translation dated Mar. 24, 2015 for Chinese Patent Application No. 201180035508X, 28 pages.
Third Chinese Office Action and English translation dated Sep. 28, 2015 for Chinese Patent Application No. 201180035508.X, 13 pages.
International Search Report and Written Opinion dated Oct. 26, 2011 for PCT/US11/37020 (International Filing Date: May 18, 2011), 11 pages.
International Search Report and Written Opinion dated Nov. 7, 2014 for PCT/US14/24650 (International Filing Date: Mar. 12, 2014), 10 pages.
U.S. Office Action dated Nov. 7, 2013 for U.S. Appl. No. 13/796,469, 13 pages.
U.S. Office Action dated Jul. 17, 2014 for U.S. Appl. No. 13/796,469, dated Jul. 17, 2014, 14 pages.
U.S. Office Action dated Sep. 17, 2012, for U.S. Appl. No. 13/110,688, 20 pages.
U.S. Office Action dated Nov. 7, 2013 for U.S. Appl. No. 13/796,527, 15 pages.
U.S. Office Action dated Jul. 18, 2014 for U.S. Appl. No. 13/796,527, 16 pages.

\* cited by examiner 1-methyl-1,4-cyclohexadiene 1,8-cineole (+)-.alpha.-methylene-.alpha.-fenchocamphorone

SYSTEM AND METHOD OF PRODUCING VOLATILE ORGANIC COMPOUNDS FROM FUNGI

CROSS REFERENCE TO RELATED APPLICATIONS

The present application is a continuation-in-part of U.S. patent application Ser. No. 13/110,688, filed May 18, 2011, now U.S. Pat. No. 8,501,458, which is entitled to priority under 35 U.S.C. §119(e) to U.S. Provisional Application No. 61/345,918, filed May 18, 2010, which applications are incorporated by reference herein in their entireties. The present application further claims the benefit of priority under 35 U.S.C. §119(e) to U.S. Provisional Application No. 61/593,671, filed Feb. 1, 2012, the entire disclosure of which is also incorporated by reference herein in its entirety.

STATEMENT REGARDING FEDERALLY SPONSORED RESEARCH OR DEVELOPMENT

This invention was made with government support under CBET-0802666 and EFRI-0937613 awarded by the National Science Foundation (NSF), and under N00244-09-1-0070 awarded by the Department of Defense (Navy). The government has certain rights in the invention.

BACKGROUND OF THE INVENTION

The identification and production of volatile organic compounds (VOCs) continues to be a driving force in the development and expansion of many commercial industries. For example, 1,8-cineole, commonly referred to as eucalyptol, is the pharmaceutically active component of *eucalyptus* oil, comprising 70-85% of the essential oil. Traditional uses of *eucalyptus* oil primarily involve non-prescription pharmaceuticals, fragrances and degreasing detergents (Opdyke, 1975, Food and Cosmetics Toxicology 13: 91-112; Hong and Shellock, 1991, American Journal of Physical Medicine and Rehabilitation 70:29-33; Leung, Y. (1980). *Eucalyptus*. New York: Wiley; Furia, T., & Bellanca, N. (1971). *Fenaroli's Handbook of Flavor Ingredients*. Cleveland, Ohio: Chemical Research Co.; Barton, et al., 1997, Chemistry in Australia 64:4-6). 1,8-Cineole also has potential applications in alternative fuel production as it has been shown to prevent phase separation when used as an additive in ethanol-gasoline fuel blends (Barton and Tjandra, 1989, Fuel 68:11-17), and alternative fuels comprised of a gasoline/*eucalyptus* oil mixture (with 1,8-cineole as the major fuel component) resulted in an improved octane number and reduced carbon monoxide exhaust (U.S. Pat. No. 4,297,109).

Also, fenchocamphorone is a derivative of fenchol via a fenchene intermediate, both of which are monoterpenes (Croteau, et al., 1988, Journal of Biological Chemistry 263:15449-15453). Fenchone, also a monoterpene of similar derivations, is a volatile compound that is found as a major constituent of fennel seed oil (Azeez, S. (2008). Fennel. In *Chemistry of Spices*, pp. 227-241. Edited by Parthasarathy, V. A., Chempakam, B., & Zachariah, T. Cambridge, Mass.: CAB International). Fennel oil is also considered an essential plant oil and is valued for its strong flavor, but is also recognized as an antioxidant, hepatoprotective agent, anti-cancer agent, and other biological activities have been described for it (Azeez 2008; Cosimi et al., 2009, Journal of Stored Products Research 45:125-132).

Another example is 1,4-cyclohexadiene, which is a highly flammable cycloalkene that yields the natural monoterpene derivative, γ-terpinene, a component associated with many essential oils. 1,4-Cyclohexadiene also readily oxidizes to benzene by a number of different methods (Breton, et al., 2005, Electrochemistry Communications 7:1445-1448; Smith and Gray, 1990, Catalysis Letters 6:195-200; Hepworth et al., 2002, Aromatic Chemistry, pp. 129-134; Brooks, B. T. (1922). The Cyclic Non-benzoid Hydrocarbons: The Cyclohexane Series. In *The Chemistry of Non-benzoid Hydrocarbons and Their Simple Derivatives*, pp. 278-383. Edited by B. T. Brooks. New York, N.Y.: Chemical Catalog Company, Inc.) which gives it multiple applications in industrial chemistry. Benzene is a natural component of crude oil and gasoline and is a widely used chemical in the production of plastics, nylon, and resins, as well as some types of rubbers, detergents, lubricants, dyes, and pesticides (Agency for Toxic Substances and Disease Registry (ATSDR) (2007). *Toxicological Profile for Benzene (Update)*. Atlanta, Ga.: U.S. Department of Public Health and Human Services, Public Health Service).

However, a major limiting factor in widespread industrial applications of these volatile compounds, particularly 1,8-cineole, pertains to its biological source. Currently, this monoterpenoid is produced solely by plants restricted to certain species of *Eucalyptus*, but also including *Rosmarinus officinalis* (Rosemary), and *Thymus valgaris* (Thyme) (Thomas, et al., 2000, Chemical Industry Digest (Special Millennium Issue) pp. 104-108), *Melaleuca teretifolia* (Southwell, et al., 2003, Journal of Essential Oil Research 15:339-341), and *Mentha spicata* (Cook, et al., 2007, The Journal of Essential Oil Research 19:225-230). A novel and more bountiful source for these compounds could significantly advance their industrial application profiles.

Endophytes, microorganisms that reside in the tissues of living plants (Stone et al., Microbial Endophytes, Ed. C. W. Bacon and J. F. White Marcel Decker, Inc, NY, 2000), are relatively unstudied and potential sources of novel natural products for exploitation in medicine, agriculture and industry. It is worthy to note, that of the nearly 300,000 plant species that exist on the earth, each individual plant is host to one or more endophytes. Only a handful of these plants have ever been completely studied relative to their endophytic biology. Consequently, the opportunity to find new and interesting endophytic microorganisms among myriads of plants in different settings, and ecosystems is great. Currently, endophytes are viewed as an outstanding source of bioactive natural products because there are so many of them occupying literally millions of unique biological niches (higher plants) growing in so many unusual environments.

It is well accepted that microorganisms can be a production source of chemical compounds, enzymes and other complexes that have industrial utility. The prospect that endophytes produce novel bioactive products stems from the idea that some endophytes may have coevolved with their respective higher plant, and as a result may produce certain phytochemicals characteristic of their hosts (Strobel and Daisy, 2003, Microbiology and Molecular Biology Reviews 67:491-502; Tan and Zou, 2001, Nat. Prod. Rep. 18:448-459). The enormous diversity generated by the presence of microbial life forms is amplified by their ability to inhabit novel niches, ranging from deep ocean sediments to the earth's thermal pools. Endophytic fungi inhabit one such biological niche and are characterized by their ability to asymptomatically colonize living plant tissues. There are untold numbers of potential novel fungal genera, of which endophytes constitute a significant proportion (Smith, et al., 2008, PloS 1 3(8):e3052). Ecosystems exhibiting the greatest plant diversity also seemingly exhibit the greatest abundance and diversity of microbial endophytes. Ultimately, biological diversity implies chemical diversity as constant chemical innovation is required in such highly competitive ecosystems. Thus, the search for novel endophytic microbes is ongoing, with activity of their natural products encompassing their use as antibiotics, antiviral compounds, anticancer agents, antioxidants, insecticides, antidiabetic agents, and immunosuppressive compounds (Strobel and Daisy, 2003, Microbiology and Molecular Biology Reviews 67:491-502).

One such endophyte is *Hypoxylon* spp., which is a fungal endophyte of *Persea indica*, an evergreen tree native to the Canary Islands, where it grows not in abundance but is found on several islands including Tenerife in the Laurisilva. *Persea* spp. are also native to Central and South America and were later introduced into Southern California (Zentmyer, et al., 1990, California Avocado Society 1990 Yearbook 74:239-242).

The complete analyses of fungal genomes in recent times indicate that many putative biosynthetic gene clusters are located in the distal regions of the chromosomes and exist in a heterochromatin state, with the constitutive genes often transcriptionally controlled by epigenetic regulation such as histone deacetylation and DNA methylation (Shwab et al., 2007, Eukaryot Cell 6:1656-1664). Several studies indicate that the inhibition of histone deacetylase activity, through gene disruption or use of epigenetic modulators, leads to the transcriptional activation of gene clusters, resulting in enhanced production of secondary metabolites (Shwab et al., 2007, Eukaryot Cell 6:1656-1664; Williams et al., 2008, Org Biomol Chem 6:1895-1897).

In fungi, both class I and class II histone deacetylases, and lysine- as well as arginine-specific methyltransferases have been identified (Brosch et al., 2008, FEMS Microbiol Rev 32:409-439). The modification of histones via acetylation and methylation reactions can have important effects on the production of fungal secondary metabolites (Shwab et al., 2007, Eukaryot Cell 6:1656-1664; Bok et al., 2009, Nat Chem Biol 5:462-464). These modifications can induce heritable epigenetic changes (Mooibroek et al., 1990, Mol Gen Genet. 222:41-48; Birch et al., 1998, J Appl Microbiol 85:417-424; Cheng et al., 2003, J Natl Cancer Inst 95:399-409). In addition, fungi treated with DNA methyltransferase and histone deacetylase inhibitors exhibited natural product profiles with enhanced chemical diversity, demonstrating that these small-molecule epigenetic modifiers are effective tools for rationally controlling the native expression of fungal biosynthetic pathways and generating biomolecules not previously known from the organism (Williams et al., 2008, Org Biomol Chem 6:1895-1897; Cichewicz, 2010, Nat Prod Rep 27:11-22). Undoubtedly, production of 1,8-cineole, among other volatile organic compounds such as 1-methyl-1,4-cyclohexadiene and (+)-α-methylene-α-fenchocamphorone by a fungal source, would have significant implications for use of such compounds in widespread industrial applications. Therefore, a need exists for the identification and production of volatile organic compounds produced by fungi. The present invention satisfies this need.

SUMMARY OF THE INVENTION

The present invention relates to a method for generating mutant strains of a fungus with an increased production rate or production amount of at least one compound selected from the group consisting of 1,8-cineole, 1-methyl-1,4-cyclohexadiene, and (+)-α-methylene-α-fenchocamphorone. The method includes mutating spores of the fungus, culturing the mutated spores, and screening the cultures of mutated spores for enhanced production rate or production amount of at least one compound selected from the group consisting of 1,8-cineole, 1-methyl-1, 4-cyclohexadiene, and (+)-α-methylene-α-fenchocamphorone. In one embodiment, the fungus is from the genus *Nodulisporium*. In a further embodiment, the fungus is from the genus *Daldinia*. In a further embodiment, the fungus is from the genus *Hypoxylon*. In a further embodiment, the fungus has the imperfect stage of *Nodulisporium*. In a further embodiment, the fungus is an isolate selected from the group consisting of Co27-5 (deposited as NRRL 50500), C14A (deposited as NRRL 50501), Ti-13 (deposited as NRRL 50502), and Ec-38 (deposited as NRRL 50503). In a further embodiment, mutating the fungus comprises contacting the fungus with a chemical modulator. In a further embodiment, the chemical modulator is suberoylanilide hydroxamic acid (SAHA). In a further embodiment, the chemical modulator is 5-azacytidine (AZA).

The present invention also relates to an isolated fungus mutated by a method for generating mutant strains of a fungus with an increased production rate or production amount of at least one compound selected from the group consisting of 1,8-cineole, 1-methyl-1,4-cyclohexadiene, and (+)-α-methylene-α-fenchocamphorone. The method includes mutating spores of the fungus, culturing the mutated spores, and screening the cultures of mutated spores for enhanced production rate or production amount of at least one compound selected from the group consisting of 1,8-cineole, 1-methyl-1,4-cyclohexadiene, and (+)-α-methylene-α-fenchocamphorone.

The present invention also relates to an isolated mutant fungus. The fungus produces at least one compound selected from the group consisting of 1,8-cineole, 1-methyl-1,4-cyclohexadiene, and (+)-α-methylene-α-fenchocamphorone in an amount that is greater than the wild type fungus of the same genus. In one embodiment, the fungus is from the genus *Nodulisporium*. In a further embodiment, the fungus is from the genus *Daldinia*. In a further embodiment, the fungus is from the genus *Hypoxylon*. In a further embodiment, the fungus has the imperfect stage of *Nodulisporium*. In a further embodiment, the fungus is an isolate selected from the group consisting of Co27-5 (deposited as NRRL 50500), C14A (deposited as NRRL 50501), Ti-13 (deposited as NRRL 50502), and Ec-38 (deposited as NRRL 50503). In a further embodiment, the fungus is mutated with a chemical modulator. In a further embodiment, the chemical modulator is suberoylanilide hydroxamic acid (SAHA). In a further embodiment, the chemical modulator is 5-azacytidine (AZA).

The present invention also includes a method for generating mutant strains of a fungus capable of producing at least one volatile organic compound (VOC) not produced by the fungus prior to mutation. The method includes contacting spores of the fungus with a chemical modulator to mutate the spores, culturing the mutated spores, and screening the cultures of mutated spores for at least one VOC which is not produced by the fungus prior to mutation. In one embodiment, the fungus is from the genus *Nodulisporium*. In a further embodiment, the fungus is from the genus *Daldinia*. In a further embodiment, the fungus is from the genus *Hypoxylon*. In a further embodiment, the fungus has the imperfect stage of *Nodulisporium*. In a further embodiment, the fungus is an isolate selected from the group consisting of Co27-5 (deposited as NRRL 50500), C14A (deposited as NRRL 50501), Ti-13 (deposited as NRRL 50502), and Ec-38 (deposited as NRRL 50503). In a further embodiment, the chemical modulator is suberoylanilide hydroxamic acid (SAHA). In a further embodiment, the chemical modulator is 5-azacytidine (AZA).

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising

DETAILED DESCRIPTION

Figure 1:
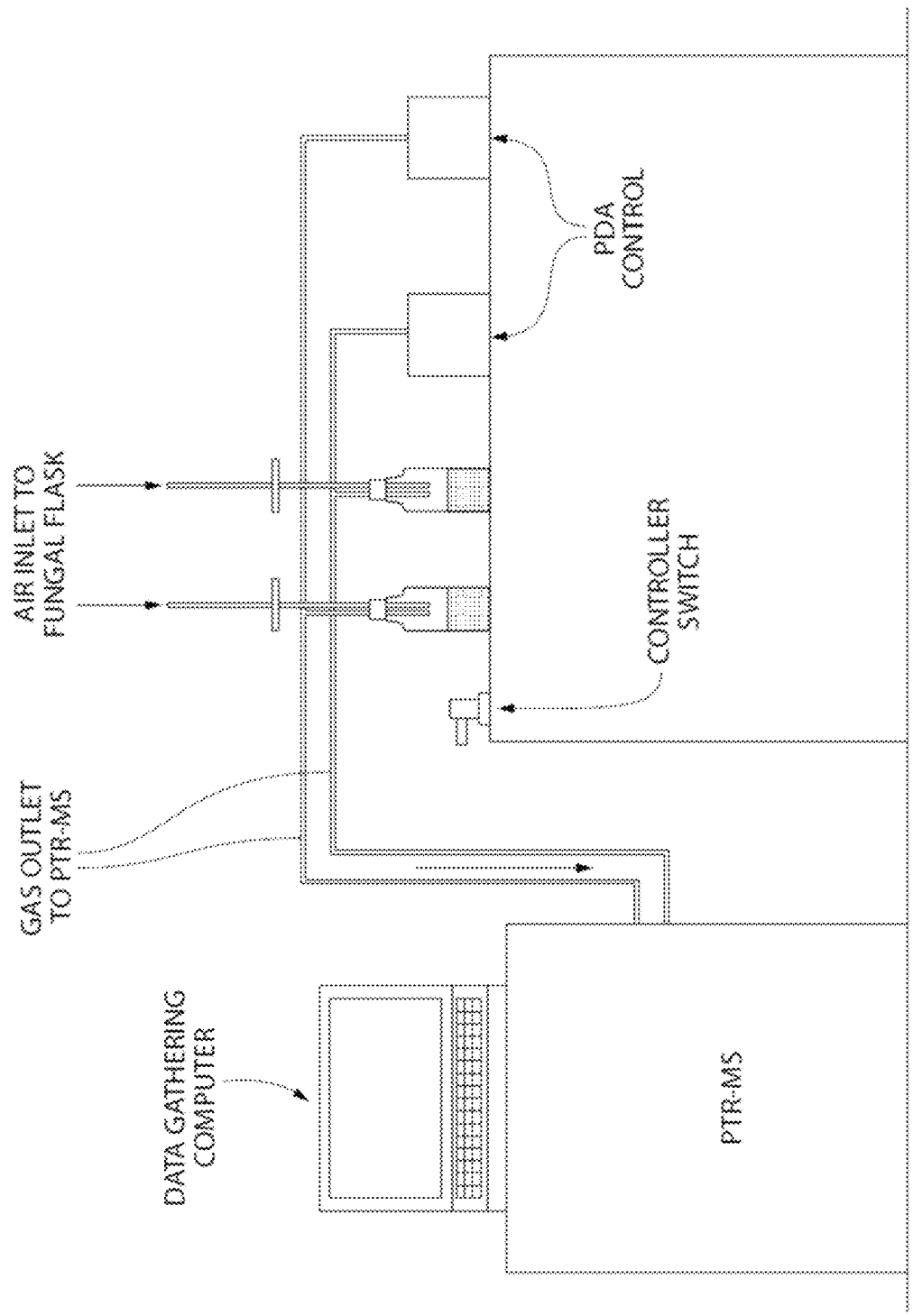
FIG. 1 depicts a PTR-mass spectrometer used to monitor VOC production by *Hypoxylon* sp. The *Hypoxylon* sp. culture produced 100.5 mg dry weight of surface mycelium covering the 121.6 $cm^2$ agar slant at 7 days. Monitoring began 2.5 days after the fungus was inoculated onto the agar surface. The inset shows the details of the hardware used to regulate gas flow into the culture flask. The controller switch continuously changes input of gases from the control bottle (only PDA) to the fungal culture. The computer screen shows the continuous output of individual ions found in the gas phase.
Figure 2A:
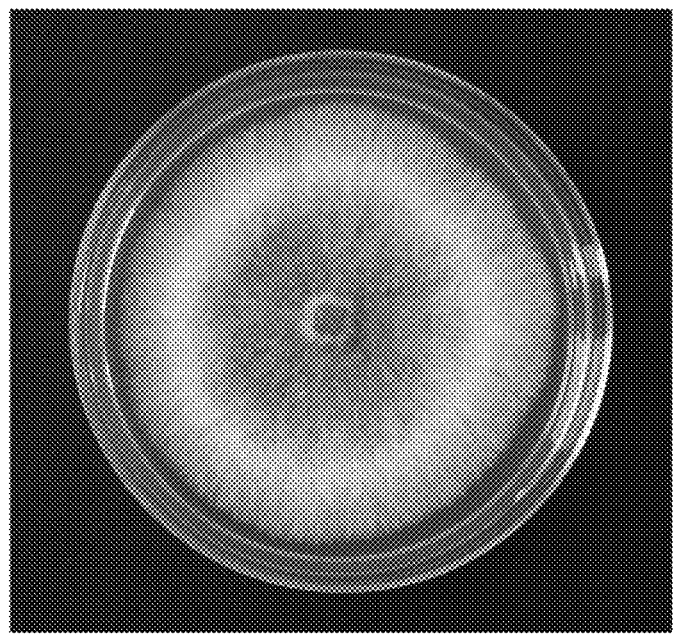
FIGS. 2A and 2B, depicts a 10-day old culture of *Hypoxylon* sp. grown on PDA from both the top side (2A) and bottom side (2B). The darker aspect of the photos represents varying degrees of a greenish-tan coloration.
Figure 2B:
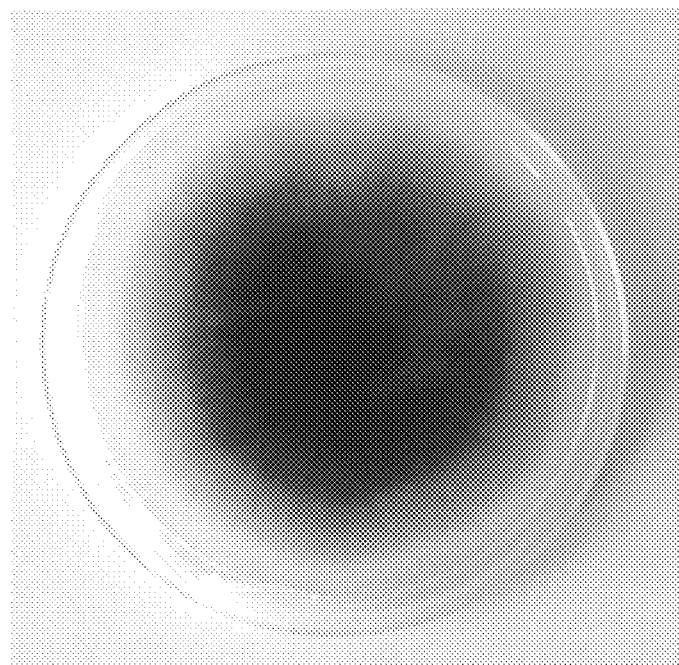
Figure 3:
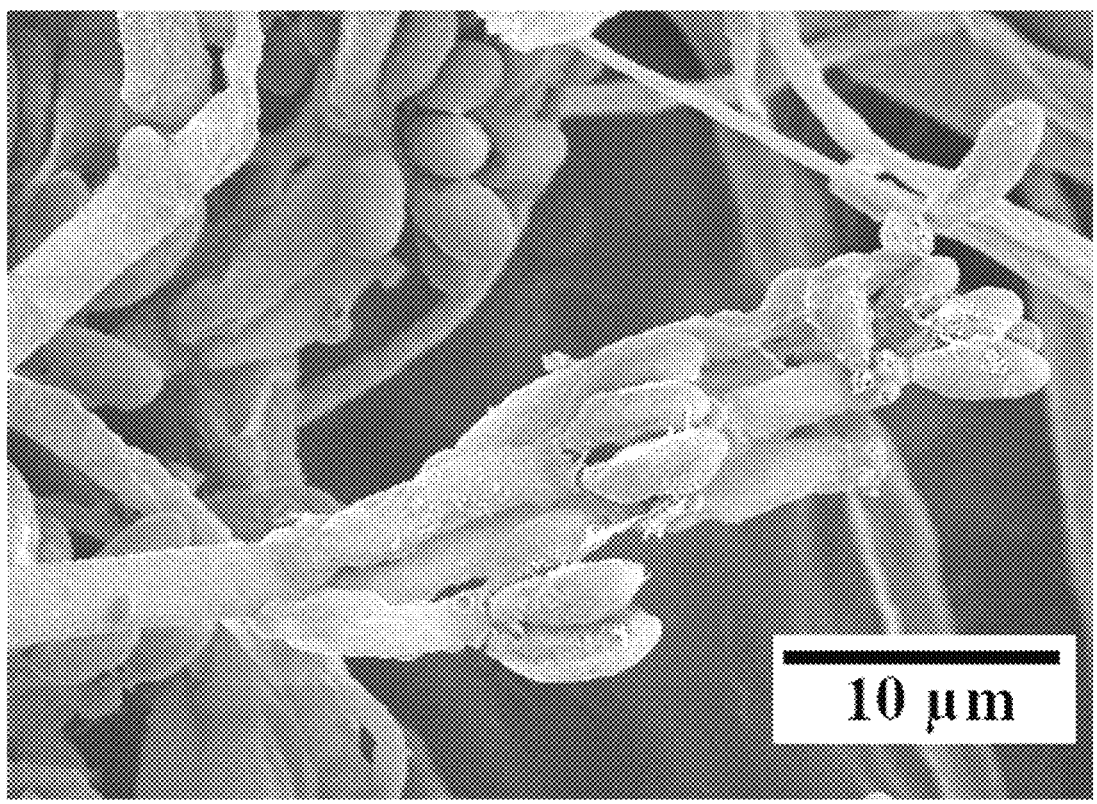
FIG. 3 is an SEM image of a branched conidiophore *Nodulisporium* sp. (CI-4) depicting conidia and scars from the budding verticles of the conidiophore.
Figure 4:
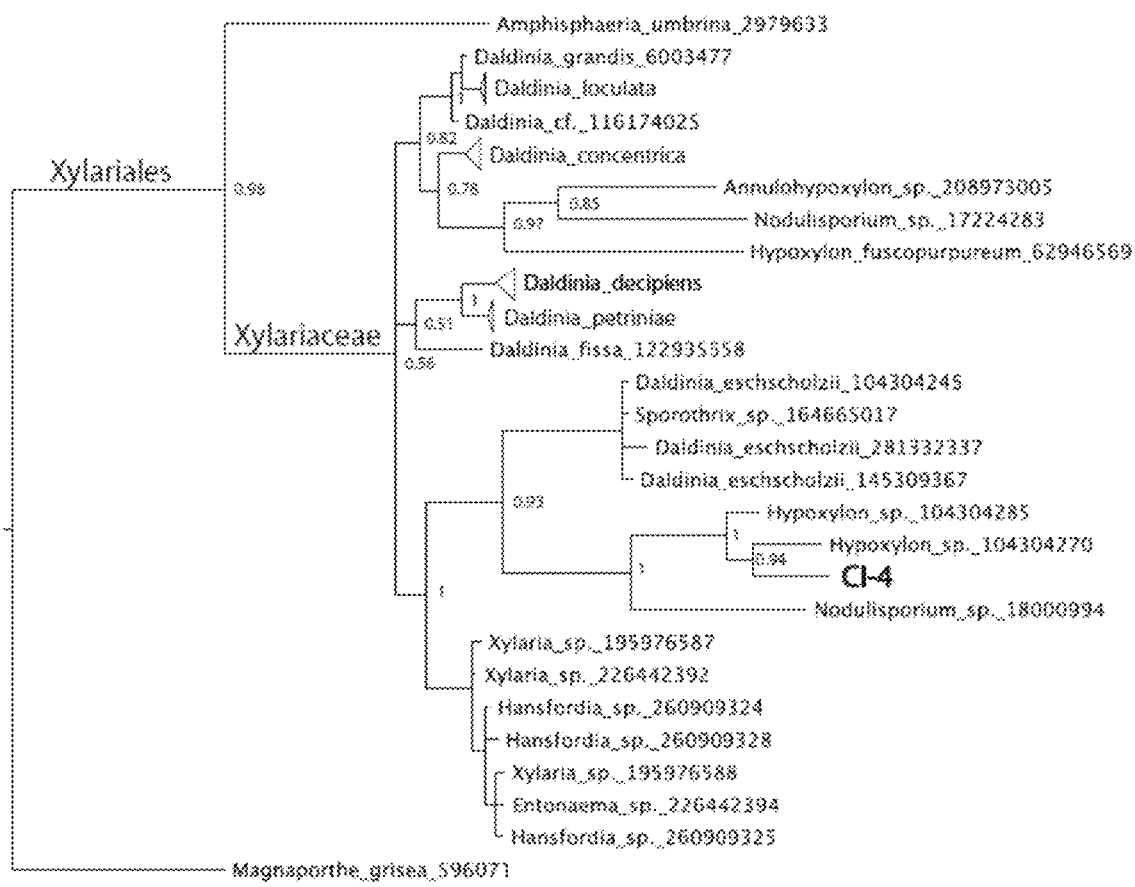
FIG. 4 is chart demonstrating the evolutionary relationships of *Hypoxylon* sp. (CI-4) with 20 other close taxons (BLAST based). The evolutionary history was inferred using the Neighbor-Joining method (Saitou and Nei, 1987, Molecular Biology and Evolution 4:406-425). The optimal tree with the sum of branch length=0.83699359 is shown. All positions containing gaps and missing data were eliminated from the dataset (complete deletion option). There were a total of 307 positions in the final dataset. Phylogenetic analyses were conducted in MEGA4 (Tamura, et al., 2007, Molecular Biology and Evolution 24:1596-1599).

The present invention relates to isolated fungal lines capable of producing an impressive spectrum of volatile organic compounds (VOCs), most notably 1,8-cineole, 1-methyl-1,4-cyclohexadiene, and (+)-α-methylene-α-fenchocamphorone, among many others (see Table 3, below). The present invention also relates to methods of producing such VOCs from fungus, and collecting or recovering the produced VOCs for commercial and/or industrial use.

The present invention is based on the discovery that selected fungi, including numerous *Hypoxylon* spp., produce an impressive spectrum of VOCs, most notably 1,8-cineole, 1-methyl-1,4-cyclohexadiene, and (+)-α-methylene-α-fenchocamphorone. Media containing starch and/or sugar related substrates best supports VOC production by fungus. Direct on-line quantification of VOCs was measured by proton transfer mass spectrometry (PTR-MS) covering a continuous range, with optimum VOC production occurring at 6 days at 145 ppmv with a rate of production of 7.65 ppmv/hr. This demonstrated that 1,8-cineole (a monoterpene) is produced by a microorganism, which represents a novel and important source of this compound. 1,8-cineole is an octane derivative and has potential use as a fuel additive, as do the other VOCs of this organism, listed in Table 3, below. Thus, fungal sourcing of this compound and other VOCs as produced by *Hypoxylon* sp. and other fungi described herein greatly expands their potential applications in medicine, industry, and energy production.

The present invention is also based on the discovery that the administration of an epigenetic modulator during growth of fungi, such as wild type CI-4 *Hypoxylon* sp., produces a novel strain of fungus. This novel fungal strain has been found to produce many of the same VOCs as the wild type strain, in addition to VOCs not produced by the wild type. Accordingly, the present invention relates to methods of producing a mutant fungus, producing such VOCs from fungus, and collecting or recovering the produced VOCs for commercial and/or industrial use.

The present invention is also based on the discovery that the administration of an epigenetic modulator during growth of fungi, such as wild type CI-4 *Hypoxylon* sp, results in the production of a variant of the wild type fungus which produces a set of VOCs different from that which is produced by the wild type strain in the absence of the epigenetic modulator. The present invention relates to methods of producing a variant of a fungus, and collecting or recovering the produced VOCs for commercial and/or industrial use.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "hydrocarbon" generally refers to a chemical compound that consists of the elements carbon (C) and hydrogen (H). All hydrocarbons consist of a carbon backbone and atoms of hydrogen attached to that backbone. Hydrocarbons are of prime economic importance because they encompass the constituents of the major fossil fuels (coal, petroleum, natural gas, etc.) and biofuels, as well as plastics, waxes, solvents and oils.

The term "fungus" or "fungi" includes a wide variety of nucleated, spore-bearing organisms that are devoid of chlorophyll. Examples of fungi include yeasts, molds, mildews, rusts, and mushrooms.

The term "bacteria" includes any prokaryotic organism that does not have a distinct nucleus.

The term "isolated" means altered or removed from the natural state or biological niche through the actions of a human being.

The term "antibiotic" includes any substance that is able to kill or inhibit a microorganism. Antibiotics may be produced by a microorganism or by a synthetic process or semisynthetic process. The term, therefore, includes a substance that inhibits or kills fungi for example, cycloheximide or nystatin.

The term "culturing" refers to the propagation of organisms on or in solid or liquid media of various kinds.

The term "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the target infection or disease states.

The term "metabolite" or "volatile" refers to any compound, substance or byproduct of a fermentation of a microorganism that has a biological activity.

The term "mutant" refers to a variant of the parental strain as well as methods for obtaining a mutant or variant in which the desired biological activity is similar to that expressed by the parental strain. The "parent strain" is defined herein as the original fungus (e.g. *Hypoxylon*) strains before mutagenesis. Mutants occur in nature without the intervention of man. They also are obtainable by treatment with or by a variety of methods and compositions understood by those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means.

The term "variant" refers to a strain having all the identifying characteristics of the strains of fungus and can be identified as having a genome that hybridizes under conditions of high stringency to the genome of the organism. A variant may also be defined as a strain having a genomic sequence that is greater than 85%, more preferably greater than 90% or more preferably greater than 95% sequence identity to the genome of the organism. A polynucleotide or polynucleotide region (or a polypeptide or polypeptide region) has a certain percentage (for example, 80%, 85%, 90%, or 95%) of "sequence identity" to another sequence, which means that, when aligned, that percentage of bases (or amino acids) are the same in comparing the two sequences. This alignment and the percent homology or sequence identity can be determined using publicly available software programs known in the art.

The term "instructional material," as that term is used herein, includes a publication, a recording, a diagram, or any other medium of expression which can be used to communicate the usefulness or procedural steps of the invention in the kit for growing the fungi under optimal conditions for optimal VOC production.

The terms "Vorinostat" and "SAHA" refer to suberoylanilide hydroxamic acid, or, N-hydroxy-N'-phenyl-octanediamide.

The terms "Entinostat" and "MS-275" refer to pyridin-3-ylmethyl 4-((2-aminophenyl)carbamoyl)benzylcarbamate.

The terms "Panobinostat" and "LBH589" refer to (E)-N-hydroxy-3-(4-((2-(2-methyl-1H-indol-3-yl)ethylamino)methyl)phenyl)acrylamide.

The terms "Trichostatin A" and "TSA" refer to (R,2E,4E)-6-(4-(dimethylamino)benzoyl)-N-hydroxy-4-methyl-hepta-2,4-dienamide.

The terms "Belinostat" and "PXD101" refer to (2E)-N-Hydroxy-3-[3-(phenylsulfamoyl)phenyl]prop-2-enamide.

The terms "Mocetinostat" and "MGCD0103" refer to N-(2-Aminophenyl)-4-[[(4-pyridin-3-ylpyrimidin-2-yl)amino]methyl]benzamide.

The term "MC1568" refers to (E)-3-(4-((E)-3-(3-fluorophenyl)-3-oxoprop-1-enyl)-1-methyl-1H-pyrrol-2-yl)-N-hydroxyacrylamide.

The terms "Romidepsin" and "FK228" refer to (1S,4S,7Z,10S,16E,21R)-7-ethylidene-4,21-diisopropyl-2-oxa-12,13-dithia-5,8,20,23-tetrazabicyclo[8.7.6]tricos-16-ene-3,6,9,19,22-pentone.

The term "M344" refers to 4-(dimethylamino)-N-(7-(hydroxyamino)-7-oxoheptyl)benzamide.

The term "P13K/HDAC inhibitor I" refers to N-hydroxy-2-(((2-(6-methoxypyridin-3-yl)-4-morpholinothieno[3,2-d]pyrimidin-6-yl)methyl)(methyl)amino)pyrimidine-5-carboxamide.

The term "PCI-34051" refers to 1-(4-methoxybenzyl)-N-hydroxy-1H-indole-6-carboxamide.

The terms "Tacedinaline" and "CI994" refer to 4-(acetylamino)-N-(2-aminophenyl)benzamide.

The term "Tubastatin A" refers to N-hydroxy-4-(2-methyl-1,2,3,4-tetrahydro-pyrido[4,3-b]indol-5-ylmethyl)-benzamide.

The terms "AR-42" and "HDAC-42" refer to (S)—N-hydroxy-4-(3-methyl-2-phenylbutanamido)benzamide.

The terms "Givinostat" and "ITF2357" refer to {6-[(diethylamino)methyl]naphthalen-2-yl}methyl [4-(hydroxycarbamoyl)phenyl]carbamate.

The terms "Pracinostat" and "SB939" refer to (E)-3-(2-butyl-1-(2-(diethylamino)ethyl)-1H-benzo[d]imidazol-5-yl)-N-hydroxyacrylamide.

The term "Droxinostat" refers to 4-(4-chloro-2-methylphenoxy)-N-hydroxybutanamide.

The term "Largazole" refers to S-{(3E)-4-[(5R,8S,11S)-8-Isopropyl-5-methyl-6,9,13-trioxo-10-oxa-3,17-dithia-7,14,19,20-tetraazatricyclo[14.2.1.1$^{2,5}$]icosa-1(18),2(20),16(19)-trien-11-yl]-3-buten-1-yl} octanethioate.

The term "CUDC-101" refers to 7-(4-(3-ethynylphenylamino)-7-methoxyquinazolin-6-yloxy)-N-hydroxyheptanamide.

The term "sodium Valproate" refers to sodium 2-propylpentanoate.

The term "JNJ-26481585" refers to N-hydroxy-2-(4-(((1-methyl-1H-indol-3-yl)methylamino)methyl)piperidin-1-yl)pyrimidine-5-carboxamide.

The terms "Dacinostat" and "LAQ824" refer to (E)-3-(4-(((2-(1H-indol-3-yl)ethyl)(2-hydroxyethyl)amino)methyl)phenyl)-N-hydroxyacrylamide.

The term "PCI-24781" refers to 3-((dimethylamino)methyl)-N-(2-(4-(hydroxycarbamoyl)phenoxy)ethyl)benzofuran-2-carboxamide.

The terms "AZA" and "5-azacytidine" refer to 4-amino-1-(β-D-ribofuranosyl)-1,3,5-triazin-2(1H)-one.

The term "Zebularine" refers to 1-(β-D-ribofuranosyl)-1,2-dihydropyrimidin-2-one.

The term "caffeic acid" refers to 3,4-dihydroxycinnamic acid.

The term "chlorogenic acid" refers to 1,3,4,5-tetrahydroxycyclohexanecarboxylic acid 3-(3,4-dihydroxycinnamate), 3-(3,4-dihydroxycinnamoyl)quinic acid.

The term "(−)-epigallocatechin gallate" refers to (−)-cis-2-(3,4,5-Trihydroxyphenyl)-3,4-dihydro-2(2H)-benzopyran-3,5,7-triol 3-gallate.

The term "hydralazine" refers to 1-hydrazinophthalazine.

The term "procainamide" refers to 4-amino-N-(2-diethylaminoethyl)benzamide.

The term "procaine" refers to 4-aminobenzoic acid 2-diethylaminoethyl ester.

The term "RG108" refers to N-phthalyl-L-tryptophan.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Further, all numerical designations, e.g., pH, temperature, time, concentration, and molecular weight, including ranges, are approximations which may be varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are well known in the art.

Fungi Suitable for Production of VOCs

A search for endophytes hosted by the evergreen tree *Persea indica* revealed the presence of a *Hypoxylon* sp., as described herein. An examination of this organism revealed that it produces important VOCs including, without limitation, 1,8-cineole; 1-methyl-1,4-cyclohexadiene, and (+)-α-methylene-α-fenchocamphorone (see Table 3, below). These compounds have potential industrial utility, such as fuels or additives as per the VOCs of some other endophytic fungi now known as Mycodiesel™ (Strobel, et al., 2008, Microbiology 154:3319-3328).

In one aspect, the present invention includes an isolated fungus capable of producing at least one VOC. For example, the following fungal isolates of *Hypoxylon*, each being capable of producing at least one VOC, were deposited under the terms of the Budapest Treaty with the ARS Culture Collection (NRRL), 1815 North University Street, Peoria, Ill. 61604-3999 USA, on May 11, 2011 and assigned the corresponding Accession Numbers:

| *Hypoxylon* sp. | NRRL Accession Number |
|---|---|
| Co27-5 | 50500 |
| CI-4A | 50501 |
| Ti-13 | 50502 |
| Ec-38 | 50503 |

These strains have been deposited under conditions that assure that access to these cultures are readily available to one determined by the Commissioner of Patents and Trademarks to be entitled thereto under 37 C.F.R. §1.14 and 35 U.S.C. §122, and are available as required by foreign patent laws in countries wherein counterparts of the subject application, or its progeny are filed. However, it should be understood that the availability of a deposit does not constitute a license to practice the subject invention in derogation of patent rights granted by governmental action. Based on these deposits, the entire genomes of *Hypoxylon* isolates Co27-5, CI-4A, Ti-13, Ec-38 or Ni-25 2A are hereby incorporated into and included in this filing.

Figure 5:
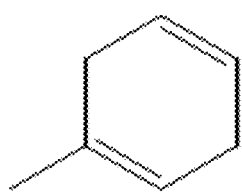
FIG. 5 is a structural depiction of the fungal volatile organic compounds I-methyl-1,4-cyclohexadiene (top left), 1,8-cineole (top right), and (+)-α-methylene-α-fenchocamphorone (bottom).
Figure 5:
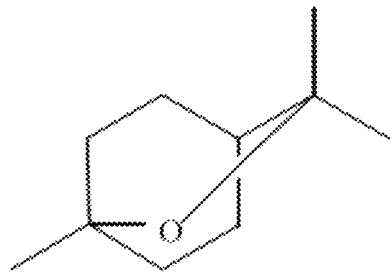
Figure 5:
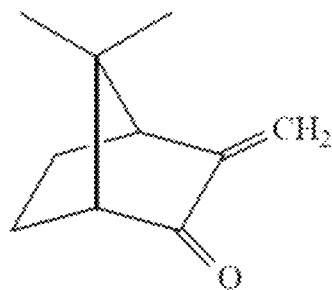

In one embodiment of the present invention, any one of the fungi described herein can produce an impressive spectrum of volatile organic compounds (see Table 3, below) including, without limitation, 1,8-cineole, 1-methyl-1,4-cyclohexadiene, and (+)-α-methylene-α-fenchocamphorone, the structures of which are depicted in FIG. 5. It should be appreciated that the present invention is not limited to production of the aforementioned VOCs by *Hypoxylon*. Rather, the present invention includes production of VOCs, particularly 1,8-cineole, 1-methyl-1,4-cyclohexadiene, and (+)-α-methylene-α-fenchocamphorone, by any fungus, or for that matter, any microorganism. For example, 1,8-cineole can also be produced by an isolated *Muscodor* sp., such as Ni5, and is therefore also contemplated as forming part of the present invention. In another example, the present invention relates to endophytic fungi that produce volatile organic compounds, such as hydrocarbons, from isolates of *Nodulisporium* spp, *Hypoxylon* spp., *Daldinia* spp. and *Muscodor* spp. These compounds produced by the fungus can then be used in a variety of commercial industries, including medicine, energy production, and fuel additives or constituents. This novel, renewable source of hydrocarbons is desirable because it provides a supplement to the existing limited resources of non-renewable hydrocarbons.

Furthermore, it should be appreciated that the disclosed *Hypoxylon* isolates can also be classified as an endophytic *Nodulisporium* sp. or *Daldinia* sp., depending on the fungal identification methodology used. Generally speaking, almost all fungi have a perfect (sexual stage) and an imperfect stage (non sexual), and each is given a name. For example, *Nodulisporium*-like organisms can have the perfect stage of *Hypoxylon, Daldinia, Xylaria* or *Annulohypoxylon*. Therefore, as contemplated herein, fungi identified as any one of *Nodulisporium* spp., *Hypoxylon* spp., and *Daldinia* spp. form part of the present invention for the generation of VOCs, as described herein. As an example of this, while strains Co27-5, CI-4A, Ti-13 and Ec-38 are generally classified as *Hypoxylon*, they each have the imperfect stage of *Nodulisporium* sp. Further, the fungi of the present invention include all anamorphs and teleomorphs, to the extent such forms exist and are available. For example, the *Hypoxylon* strains Co27-5, CI-4A, Ti-13 and Ec-38 have *Nodulisporium* sp. as their anamorphic stage. The difference between an anamorph and teleomorph is that one is the asexual state and the other is the sexual state, where the two states exhibit different morphology under certain conditions.

In cases where fungi reproduce both sexually and asexually, these fungi may have two names. For example, the teleomorph name describes the fungus when reproducing sexually, while the anamorph name refers to the fungus when reproducing asexually. Also, the holomorph name refers to the "whole fungus", encompassing both reproduction methods. When referring to any one of these names as describing a fungus, all such fungal stages or forms are contemplated and included in the present invention, regardless of whether a different or alternative name may exist. Thus, it should be appreciated that for the aforementioned *Nodulisporium* spp., *Hypoxylon* spp. and *Daldinia* spp., and even *Muscodor* spp., and synonyms thereof, the present invention encompasses both the perfect and imperfect ("anamorph") states, and other taxonomic equivalents, e.g., teleomorphs, regardless of the species name by which they are called. Those skilled in the art will readily recognize the identity of appropriate equivalents.

As will be appreciated by one of skill in the art, microorganisms such *Nodulisporium* spp., *Hypoxylon* spp., *Daldinia* spp. and *Muscodor* spp. can be used in combination with other microbes (e.g. yeasts or other bacteria) for the large scale production of biofuels.

As contemplated herein, the present invention also includes isolated strains of a *Nodulisporium, Hypoxylon, Daldinia* or *Muscodor*, wherein the isolated fungal strain was serially propagated. When strains are serially propagated, some of the characteristics of the strain may change. Such changes include deletion or suppression of metabolic pathways, an increase in certain metabolic pathways, changes to the chromosome, genes and/or operons (e.g. via mutations or changes in the regulatory factors that control the expression level of said genes or operons). For example, a strain of *Hypoxylon* may have changes in its metabolic characteristic and/or genetic make-up as compared to *Hypoxylon* isolates Co27-5, C14A, Ti-13, Ec-38 or Ni-25 2A. Such changes to the metabolic characteristics and/or genetic make-up may increase and/or decrease the production of the specific compounds listed in Table 3. Methods for isolating mutant cells with a desired characteristic are well known in the art. See, for example, U.S. Pat. No. 5,348,872, which is herein incorporated by reference in its entirety.

The present invention also provides a method for producing volatile organic compounds, such as hydrocarbons. In one embodiment, the method comprises culturing isolates of *Nodulisporium* spp, *Hypoxylon* spp., *Daldinia* spp. and *Muscodor* spp. under conditions sufficient for producing VOCs, and collecting or recovering the produced VOCs. The methods of the present invention also include any combination of procedures and steps used in the culturing of fungi and recovery of at least one VOC, as described hereinthroughout.

Volatile Organic Compounds Produced by Fungi

As stated previously, the present invention relates to endophytic fungi that produce volatile organic compounds, such as the hydrocarbons listed in Tables 3 and 8, below. Of particular interest is the production of 1,8-cineole, 1-methyl-1,4-cyclohexadiene, and (+)-α-methylene-α-fenchocamphorone, the structures of which are depicted in FIG. 5. Each of these compounds is either itself a monoterpene or is a direct derivative of a monoterpenic compound. Given that monoterpenes are prime constituents of essential plant oils, production of such compounds by an endophytic fungus may lie in support of the idea that as these fungi coevolved with their respective higher plant hosts there was a gene transfer resulting in the production of characteristic host phytochemicals (Strobel and Daisy, 2003, Microbiology and Molecular Biology Reviews 67:491-502). Whether or not this is consistent for this particular endophyte, 1,8-cineole is not known to be a constituent of essential oils collected from leaves of a *Persea indica* plant in California (Weyerstahl, et al., 1993, Flavour and Fragrance Journal 8:201-207). However, this possibility should not be disregarded, given the highly diverse environment of this isolate. The ability of *Hypoxylon* sp. to synthesize monoterpenic compounds typically associated with antimicrobial activity exemplifies the ability for microorganisms to inhabit essential oil producing plants, and their potential role in acquiring the biosynthetic pathways of these compounds should not be overlooked (Table 2).

1,8 Cineole has a broad spectrum of uses, from over-the-counter medical ointment to solvent/degreasers to flavoring/fragrances to alternative fuel. Thus, production of 1,8-cineole by a fungal isolate is significant and greatly expands its potential for a broad spectrum of industrial applications. For example, previous studies have shown prevention of phase separation when 1,8-cineole is used as an additive in ethanol-gasoline fuel blends (Barton and Tjandra, 1989, Fuel 68:11-17), and alternative fuels comprised of a gasoline/*eucalyptus* oil mixture, with 1,8-cineole as the major fuel component, resulted in an improved octane number and reduced carbon monoxide exhaust (Sugito, K., & Takeda, S. (1981). U.S. Pat. No. 4,297,109).

In certain embodiments, the VOCs may be hydrocarbons, and may be useful for the production of biofuels, plastics, plasticizers, antibiotics, rubber, fuel additives, and/or adhesives.

As will be appreciated by one of skill in the art, hydrocarbons can also be used for electrical power generation and heating. The chemical, petrochemical, plastics and rubber industries are also dependent upon hydrocarbons as raw materials for their products. As used herein, the term "biofuel" refers generally to any fuel that derives from biomass, i.e. recently living organisms or their metabolic byproducts, such as manure from cows, or a hydrocarbon produced by fungi. A biofuel may be further defined as a fuel derived from a metabolic product of a living organism.

While the production of other monoterpenes like citronellol, geraniol, linalool, nerol, and α-terpinol by microorganisms such as *Ceratocystis* spp., *Trametes odorata, Phellinus* spp., and *Kluyveromyces lactis* (Kempler, G. M. (1983). Production of Flavor Compounds by Microorganisms. III. Terpenenes. B. Production of Monoterpenes by Microorganisms. In *Advances in Applied Microbiology*, Vol 29, pp. 35-37. Edited by A. I. Laskin. New York, N.Y.: Academic Press, Inc.) has been demonstrated, the present invention represents the first time that 1,8-cineole and the other volatile products listed in Table 3 can be produced by endophytic fungi. Prior to this, the only known biological source of 1,8-cineole was from plant tissue. Production of VOCs from fungi represents a far superior commercial production model than from plants.

Biosynthesis of 1,8-cineole involves its conversion from geranyl pyrophosphate by 1,8-cineole cyclase (cineole synthase), whose activity is inhibited by cysteine- and histidine-directed reagents but protected by substrate-metal ion complexes, with the ether oxygen atom of this oxygen-containing terpene being solely derived from water (Croteau, et al., 1994, Arch-Biochem-Biophys 309:184-192). In comparison, fenchocamphorone is also converted from geranyl pyrophosphate and proceeds through the pathway as the intermediate (−)-(3R)-linalyl pyrophosphate via (−)-endo-fenchol cyclase (synthase) which subsequently cyclizes in the presence of the (4R)-α-terpinyl and (1R,5R)- pinyl cations to form (−)-endo-Fenchol which can further oxidize to α/β-fenchocamphorone (Croteau, et al., 1988, Journal of Biological Chemistry 263:15449-15453). An understanding of these individual pathways and their derivation from a common pathway involving production of geranyl pyrophosphate from mevalonate (MVA pathway) agrees with the idea that *Hypoxylon* sp. may be conditioned for biosynthesis of monoterpenes and subsequent manipulation of these pathways could lead to their optimum production on a mass commercial scale.

Growth Substrates and Culturing of Fungi for Production of VOCs

It should be appreciated that any substrate suitable for promoting fungal growth may be used in the production of VOCs, including without limitation any of the components listed in Table 4, in any ratios and combinations, as would be understood by those skilled in the art. As contemplated herein, high starch substrates promote optimal VOC production, as demonstrated by substrate utilization assays containing high amounts of starch as a carbohydrate source (Table 4). In certain embodiments, cellulose may also be a suitable substrate. Given the enormous volumes of accumulating cellulitic biomass and the utilization of foodstuff grains in alcohol (fuel) production, microorganisms that utilize cellulose for the production of VOCs are quite attractive.

For example, in some embodiments, the culture media for culturing fungi may include substrates comprising oatmeal, barley, or potato agar bases. The culture media may also be a PDA medium, a cellulose medium, and may include starch, glucose, or any combination of components listed in Table 4. Further, the selected fungal strain may be grown in a medium containing any combination of inorganic salts, organic nitrogen sources, such as peptones, defatted cotton seed flour, corn steep liquor, or yeast extract and carbon source. Examples of carbon source may include, but is not limited to, glucose, lactose, sucrose, cellulose or other carbohydrates. Further still, it should be appreciated that the present invention should not be limited by the type or amount of growth media used, and should include use of any media suitable for cultivating fungi as would be understood by those skilled in the art. In other embodiments, these conditions can also include culturing fungi in the absence of oxygen (anaerobic conditions) or in reduced oxygen conditions (e.g., microaerophilic conditions).

Generally speaking, the isolated fungi of the present invention can be cultured using standard methods as would be understood by those skilled in the art. Alternatively the fungal cultures can be cultured on a large scale for commercial use, by using conventional fermentation techniques. In this context fermentation is used broadly to refer to any controlled fungal culturing conditions. Prior to large scale growth an inoculum of said growth culture is generally cultured. In certain embodiments, the fungi can be cultured in a bioreactor vessel for a scaled up production of VOCs. Any conventional bioreactor vessel can be used as the vessel for the purpose of this invention. For example, the vessel may be made of materials such as stainless steel, glass, plastic, and/or ceramics, and may have a volume of from about 100 ml to 10,000 L or larger. The bioreactor vessel may be connected to a series of storage flasks that contain nutrient solutions and solutions for maintaining and controlling various parameters of the cultivation and VOC recovery process. Depending on the particular needs of the fermentation, there may be separate storage flasks for individual supply of substrates to the vessel, which substrates serve as the carbon, nitrogen or mineral source for the living cells in the vessel.

Further, several methods can be used to grow the various fungal isolates for use in the invention. Fed Batch culture is a variation on ordinary batch culture and involves the addition of a nutrient feed to the batch. Cells are cultured in a medium in a fixed volume. Before the maximum cell concentration is reached, specific supplementary nutrients are added to the culture. The volume of the feed is minimal compared to the volume of the culture. Fed batch culture typically proceeds in a substantially fixed volume, for a fixed duration, and with a single harvest either when the cells have died or at an earlier, predetermined point.

In a continuous culture, the cells are initially grown in a fixed volume of medium. To avoid the onset of the decline phase, fresh medium is pumped into the bioreactor before maximum cell concentration is reached. The spent media, containing a proportion of the cells, is continuously removed from the bioreactor to maintain a constant volume. The process also removes the desired product, which can be continuously harvested, and provides a continuous supply of nutrients, which allows the cells to be maintained in an exponentially growing state. Theoretically, the process can be operated indefinitely. Continuous culture is characterized by a continuous increase in culture volume, an increase and dilution of the desired product, and continuous maintenance of an exponentially growing culture.

Perfusion culture is similar to continuous culture except that, when the medium is pumped out of the reactor, cells are not removed. As with a continuous culture, perfusion culture is an increasing-volume system with continuous harvest that theoretically can continue indefinitely.

Recovery of VOCs

Once produced by the selected fungi isolate, several methods can be used to isolate the VOCs listed in Table 3 from the culture media or from vapor in a growth chamber. For example, common separation techniques can be used to remove the cells from the broth or agar, and common isolation procedures, such as (without limitation) extraction, distillation, and carbocolumn trap procedures, can be used to obtain VOCs from the cell-free broth or agar. See, for example, U.S. Pat. Nos. 4,275,234, 5,510,526; 5,641,406, and 5,831,122, and International Patent Application Number WO 93/00440, each of which is hereby incorporated by reference in its entirety.

Fractional distillation and/or absorption chromatography are also non-limiting examples of methods to extract the desired product produced by fungal isolates of the present invention. Fractional distillation is the separation of a mixture into its component parts, or fractions, such as in separating chemical compounds by their boiling point by heating them to a temperature at which several fractions of the compound will evaporate. Absorption chromatography is a physical separation method in which the components of a mixture are separated by differences in their distribution between two phases, one of which is stationary (stationary phase) while the other (the mobile phase) moves through it in a definite direction. The substances must interact with the stationary phase to be retained and separated by it.

Gas chromatography is a well known technique for fractionating and determining the relative amounts of various components in a sample containing a mixture of compounds of differing volatilities. For example, the sample is vaporized and the entire resulting quantity of gases is passed through an analytical chromatography column. Chromatographic processes such as gas chromatography can rapidly determine the volatiles content of a multicomponent sample, such as would be produced by the fungal isolates of the present invention.

In some instances, Pressure Swing Adsorption (PSA) may be used to separate some gas species from a mixture of gases under pressure according to the species' molecular characteristics and affinity for an adsorbent material. It operates at near-ambient temperatures and so differs from cryogenic distillation techniques of gas separation. Special adsorptive materials (e.g., zeolites) are used as a molecular sieve, preferentially adsorbing the target gas species at high pressure. The process then swings to low pressure to desorb the adsorbent material.

As contemplated herein, a carbotrap column may be used for the trapping and recovery of VOCs. Generally, VOCs produced by a fungal culture pass through a trapping column containing adsorption material, and are trapped within the column as they are captured by the adsorption material. The VOCs may then be released from the trapping column by simultaneously heating the column while purging with a gas, and collecting the VOCs in a cold trap condenser. A detailed description can be found in U.S. patent application Ser. No. 13/591,968, which is hereby incorporated by reference in its entirety.

Mutant and/or Engineered Fungi for Enhanced Production of VOCs

The present invention also includes mutant or engineered fungi that ultimately increase the production yield of at least one VOC, or the speed at which the mutant or engineered fungi can produce at least one VOC. Mutant or engineered fungi are obtainable by treatment of fungi with or by a variety of methods and compositions understood by those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means.

For example, as contemplated herein, the present invention also includes identifying and cloning genes that encode for production of at least one VOC from the genomes of each fungus described herein. In one embodiment, the *Hypoxylon* genome is probed for the gene or genes (e.g. an operon) that encode the synthetic pathways that produce a VOC from Table 3, such as 1,8-cineole, 1-methyl-1,4-cyclohexadiene, and (+)-α-methylene-α-fenchocamphorone. Thus, the present invention encompasses an isolated nucleic acid molecule from fungi encoding a polypeptide involved in the synthesis or production of at least one VOC. In another embodiment, an isolated nucleic acid molecule is at least 65%, at least 70%, at least 75%, at least 80%, at least 85%, at least 90%, at least 95%, at least 96%, at least 97%, at least 98%, or at least 99% identical to said isolated nucleic acid molecule from any one of the fungi isolates described herein. In another embodiment, a polypeptide sequence is at least 65%, at least 70%, at least 75%, at least 80%, at least 85%, at least 90%, at least 95%, at least 96%, at least 97%, at least 98%, or at least 99% identical to a polypeptide from any one of the fungi isolates described herein.

Methods to clone and/or probe genomes for synthetic pathways may include creating cDNA and/or genomic libraries, and screening the libraries for genes that produce the VOC synthetic pathways. Thus, the present invention comprises a DNA and/or chromosomal library of any one of the fungi isolates described herein. In one embodiment, the library is cloned into a vector that can replicate in a prokaryotic cell and/or eukaryotic cell. In another embodiment, the eukaryotic cell is a fungal cell. In another embodiment, the library is a lambda phage, Yeast Artificial Chromosome, Bacterial Artificial Chromosome, and/or cDNA. In another embodiment, the library is screened for production of VOCs from Table 3, such as 1,8-cineole, 1-methyl-1,4-cyclohexadiene, and (+)-α-methylene-α-fenchocamphorone.

Another method for determining the gene, genes and/or operon(s) that encode for the production of VOCs include mutagenizing the genome of any one of the fungi described herein and looking for an increase, addition, reduction or removal of a specific VOC. This can be accomplished via chemical and/or transposon mutagenesis. Once a gene, genes and/or operon(s) is identified, said gene, genes or operon(s) can be cloned and/or isolated. Thus, one embodiment of the invention comprises an isolated nucleic acid of any one of the fungi described herein, wherein the nucleic acid molecule is cloned into a vector. In another embodiment, said nucleic acid molecule encodes for a gene, genes, or operon(s) that encode for proteins involved in the production of VOCs of Table 3. In another embodiment, the vector autonomously replicates or integrates into the host's chromosome. In another embodiment, said vector is transformed or transfected into a heterologous cell. In another embodiment, said heterologous cell is selected from the group consisting of a prokaryotic or eukaryotic cell.

The present invention also encompasses variants and fragments of polynucleotides and/or proteins of any one of the fungi described herein that produce or are part of the pathway(s) that produce VOCs. The variants may contain alterations in the nucleotide and/or amino acid sequences of the constituent proteins. The term "variant" with respect to a polypeptide refers to an amino acid sequence that is altered by one or more amino acids with respect to a reference sequence. The variant can have "conservative" changes, or "nonconservative" changes, e.g., analogous minor variations can also include amino acid deletions or insertions, or both. In addition, the nucleotides can be sequenced to ensure that the correct coding regions were cloned and do not contain any unwanted mutations.

Nucleic acid molecules encoding one or more biosynthetic enzyme or protein, and orthologs and homologs of these sequences, may be incorporated into transformation or expression vectors of any one of the fungi described herein. As used herein, the term "vector" refers generally to a nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. A transformed cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Once the gene(s) and/or operon(s) of any one of the fungi described herein have been identified, cloned, transformed, transfected or infected into a heterologous organism (or new organism from a synthetic genome), the heterologous organism can be grown to produce and purify the desired VOCs, including those listed in Table 3.

Thus, the present invention also includes a method for generating mutant strains of a fungus with an increased production rate or production amount of at least one compound, such as 1,8-cineole, 1-methyl-1,4-cyclohexadiene, and (+)-α-methylene-α-fenchocamphorone, or any other compound listed in Table 3, below. The method includes the steps of mutating spores of the fungus, culturing the mutated spores, and screening the cultures of mutated spores for enhanced production rate or production amount of at least one compound selected from the group consisting of 1,8-cineole, 1-methyl-1,4-cyclohexadiene, and (+)-α-methylene-α-fenchocamphorone.

Other non-limiting examples include media engineering and optimization of growth conditions, co-culture, genetic manipulation, and epigenetic modulation. A mutant strain of a fungus is desirable because it may produce new molecules and overproduce other secondary metabolites in comparison to the wild type strain. In some embodiments, the mutant strain produces a VOC which is not produced by the parent strain. In some embodiments, the mutant strain produces a VOC in a larger quantity than that produced by the parent strain. In some embodiments, the mutant strain does not produce a VOC which is produced by the parent strain. VOCs produced by a mutant strain may be produced and recovered, as described elsewhere herein.

In some embodiments, a modulator is added during growth to the parent strain of a fungus, thereby generating a mutant strain. In one embodiment, the modulator is an epigenetic modulator. Epigenetic modulators are known in the art to play a role in DNA methylation and chromatin remodelling, i.e. in DNA winding and/or unwinding, thereby modulating gene expression. Epigenetic modifiers can be used as effective tools for rationally controlling the native expression of fungal biosynthetic pathways and generating biomolecules not previously known from the organism. Any epigenetic modulator known in the art is contemplated for use in the methods of the present invention. For example, histone deacetylase inhibitors (HDACs) and DNA methyltransferase inhibitors may be used as epigenetic modulators. Examples of HDACs include, but are not limited to, SAHA (Vorinostat), Entinostat (MS-275), Panobinostat (LBH589), Trichostatin A (TSA), Belinostat (PXD101), Mocetinostat (MGCD0103), MC1568, Romidepsin (FK228), M344, P13K/HDAC inhibitor I, PCI-34051, Tacedinaline (CI994), Tubastatin A, AR-42 (HDAC-42), Givinostat (ITF2357), Pracinostat (SB939), Droxinostat, Largazole, CUDC-101, sodium Valproate, JNJ-26481585, Dacinostat (LAQ824), and PCI-24781. Examples of DNA methyltransferase inhibitors include, but are not limited to, AZA (5-azacytidine), Zebularine, caffeic acid, chlorogenic acid, (−)-epigallocatechin gallate, hydralazine, procainamide, procaine, and RG108. In one embodiment, the epigenetic modulator is SAHA. In one embodiment, the epigenetic modulator is AZA.

Also contemplated herein are methods for modulating the production of VOCs produced by a fungus. These methods provide a variant of a parent strain of a fungus, wherein the variant produces a different set of VOCs from that of the parent strain. The variant strain is different from a mutant strain, as the variant strain will regain characteristics and bioactivity of the parent strain when the method of modulation is absent. The modulation may result in the production of a new VOC not produced by the wild type strain, and/or the increased production of a VOC which is produced by the parent strain. In some embodiments, the variant strain produces a VOC which is not produced by the parent strain. In some embodiments, the variant strain produces a VOC in a larger quantity than that produced by the parent strain. In some embodiments, the variant strain does not produce a VOC which is produced by the parent strain. VOCs produced by a variant strain may be produced and recovered, as described elsewhere herein. A variant may be generated by any method known in the art. In some embodiments, variants are generated by the administration of a modulator to the parent strain during growth. In one embodiment, the modulator is an epigenetic modulator. Examples of epigenetic modulators, such as HDACs and DNA methyltransferase inhibitors, are described elsewhere herein. In one embodiment, the epigenetic modulator is SAHA. In one embodiment, the epigenetic modulator is AZA.

Kits

The present invention also provides for a kit comprising one or more containers filled with one or more of the ingredients of the compositions of the invention. The present invention provides kits that can be used in any of the methods described herein. In one embodiment, a kit comprises at least one *Nodulisporium* sp., *Hypoxylon* sp., *Daldinia* sp. or *Muscodor* sp., in one or more containers. The organism can be supplied frozen in media, freeze dried and/or as spores. The kit may also include instructional material for growing the fungi under optimal conditions for optimal VOC production. The methods in the instructions may include specific bioreactor volumes, purification schemes, optimal temperature, pH, and/or other conditions. The kit may also include the growth media. The media contained in the containers of these kits may be present as a ready-to-use formulation, or as a more concentrated formulation. In addition, the media can be supplied in dry powder. Thus, a kit can comprise a dry power of the media of the invention and a liquid to suspend the media. The liquid may be water or buffers known in the art. Filters for sterilization of the media may also be provided.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way any portion of the disclosure.

Example 1: *Hypoxylon* sp, an Endophyte of *Persea indica*, Producing 1,8-Cineole and Other Bioactive Volatiles with Fuel Potential Fungal Isolation and Storage Endophytic fungal culture, CI-4, was obtained as an endophyte from an evergreen tree (*Persea indica*), native to the Canary Islands. One small limb was excised from *Persea indica* found growing on the island of Tenerife, Spain, at N—28° 32' 23"; W—16° 16' 16". Other plant species sampled from this same island included *Acacia* sp., *Pinus canariensis, Prunus lusitanica* and *Rhamnus glandifolia*, none of which fostered recovery of CI-4. Isolation procedures followed a previously described protocol (Worapong, et al., 2001, *Cinnamomun zeylanicum*. Mycotaxon 79:67-79; Ezra, et al., 2004, Microbiology 150:4023-4031). Briefly, external tissues were thoroughly exposed to 70% ethanol prior to excision of internal tissues which were cultured on standard Petri dishes of water agar and glycerol arginine medium (GAM). Endophytic fungi growing from the plant tissues were then picked and re-cultured on potato dextrose agar (PDA). It is also notable that CI-4 grows readily in the presence of the VOCs of M. albus, which should facilate its ready isolation from other plant sources (Strobel, et al., 2001, Microbiology 147:2943-2950). The fungus was stored by placing small plugs of PDA supporting mycelial growth in 15% glycerol at −70° C. An alternative storage method was also utilized in which the fungus colonized sterile barley seed, which was subsequently air dried and then stored at −70° C.

Scanning Electron Microscopy

Scanning electron microscopy (SEM) was performed on sterile carnation leaves colonized with CI-4. according to the following protocol outlined by Ezra (Ezra, et al., 2004, Microbiology 150:4023-4031). The fungus was grown on PDA, or gamma irradiated carnation leaves for several weeks and then was processed for SEM. The samples were slowly dehydrated in ethanol and then critically point dried, coated with gold and examined with an FEI XL30 scanning electron microscope (SEM) FEG with high vacuum mode using an Everhart-Thornley detector.

Fungal DNA Isolation and Acquisition of ITS-5.8S rDNA Phylogenetics

The fungus was grown on PD broth for 7 days, after which the mycelium was harvested and the genomic DNA extracted using DNeasy Plant and Fungi Mini Kit (Qiagen), according to the manufacturer's directions. The internal transcribed spacer (ITS) regions of the fungus were amplified using PCR with the universal ITS primers ITS1 (5' TCC GTA GGT GAA CCT GCG G 3') (SEQ ID NO:1) and ITS4 (5' TCC TCC GCT TAT TGA TAT GC 3') (SEQ ID NO:2). All other procedures were carried out as previously described by Ezra. The DNA was sequenced and submitted to GenBank. Sequences obtained in this study were compared to the GenBank database using the BLAST software. A phylogenetic tree was assembled using MEGA4 (Tamura, et al., 2007, Molecular Biology and Evolution 24:1596-1599) and the Neighbor-Joining method (Saitou and Nei, 1987, Molecular Biology and Evolution 4:406-425) with positions containing gaps and missing data eliminated from the dataset (complete deletion option).

Bioassay Tests for Hypoxylon sp. VOCs Against Pathogens

The VOCs produced by CI-4 were tested for inhibitory antimicrobial activity against selected pathogenic fungi and bacteria according to a bioassay test system previously described for analysis of VOCs produced by Muscodor albus (Strobel, et al., 2001, Microbiology 147:2943-2950). Optimum production of volatile bioactive compounds was determined by exposing test organisms to cultures of varying ages. Inhibitory activities of the VOCs produced by CI-4 after 3-7 days were compared and maximum inhibition observed would suggest the highest concentration of bioactive VOCs. Subsequent bioassay tests were conducted on a wider range of test organisms at the appropriate point at which CI-4 produced maximal amounts of bioactive VOCs.

The assays were conducted by removing a 2.5 cm wide strip of agar from the mid-portion of a standard Petri plate of PDA, creating two isolated halves of agar. The fungus (CI-4) was inoculated onto one half-moon agar piece and incubated at 23° C. for six days to allow for optimum production of volatile compounds. Test pathogens were inoculated onto the half-moon section of agar opposite the half-moon section inoculated with CI-4. The plate was then wrapped with a single piece of Parafilm and incubated at 23° C. for 24 hours. Growth of yeast and bacteria was then qualitatively assessed based on microbial density of a streak inoculum, while growth of filamentous fungi was quantitatively assessed based on multiple measurements of growth extending from the edge of the inoculum plugs comparable to corresponding controls as described by Strobel (Strobel, et al., 2001, Microbiology 147:2943-2950). Ultimately, viability of each test pathogen for which growth was not observed was evaluated after three days of exposure to CI-4 VOCs by transfer of the original exposed inoculum plug or streak onto a fresh plate of PDA. Viability was then determined via observation of growth within three days (Strobel, et al., 2001, Microbiology 147:2943-2950). All tests were conducted in triplicate.

Media Selection for Preferred Substrate Utilization Assay for VOC Production

A variety of selected media was used to determine a combination of substrates that best facilitated VOC production by CI-4. A single plug taken from an actively growing culture of CI-4 on PDA was used to inoculate each agar based medium. Preliminary quantification of 1,8 cineole was estimated by a human olfactory method since this compound is readily sensed by smell. Independent ratings given on a 7 day old cultures grown at 22° C., that had been sealed with parafilm, by seven different observers on two separate occasions. The rating system was 1 (low to none) up to 5 (maximum production). The evaluations were averaged and the standard deviations calculated.

The amount of fungal mycelial growth was assessed by scraping it directly from the surface of the agar surface, drying, and weighing. The following media were tested: (A) yeast extract 0.1 g $l^{-1}$ plus salts; (B) peptone 0.1 g $l^{-1}$ plus salts; (C) cellulose 25 g $l^{-1}$ plus salts and yeast extract 0.1 g $l^{-1}$; (D) cellulose 25 g $l^{-1}$ plus salts and peptone 0.1 g $l^{-1}$; (E) starch 25 g $l^{-1}$ plus salts and yeast extract 0.1 g $l^{-1}$; (F) starch 25 g $l^{-1}$ plus salts and peptone 0.1 g $l^{-1}$; (G) glucose 25 g $l^{-1}$ plus salts and yeast extract 0.1 g $l^{-1}$; (H) glucose 25 g $l^{-1}$ plus salts and peptone 0.1 g $l^{-1}$; (I) cellobiose 25 g $l^{-1}$ plus salts and yeast extract 0.1 g $l^{-1}$; (J) cellobiose 25 g $l^{-1}$ plus salts and peptone 0.1 g $l^{-1}$; (K) glycerol 25 ml $l^{-1}$ plus salts and yeast extract 0.1 g $l^{-1}$; (L) glycerol 25 ml $l^{-1}$ plus salts and peptone 0.1 g $l^{-1}$; (M) instant mashed potatoes 25 g $l^{-1}$ plus salts and yeast extract 0.1 g $l^{-1}$(MP); (N) potato dextrose (Difco) (PDA); and (O) oatmeal agar (Difco). The salts and agar concentration used in each medium followed the recipe of the M1-D medium previously outlined by Pinkerton & Strobel (Pinkerton and Strobel, 1976, Proc Natl Acad Sci USA 73:4007-4011). Each assay was performed in duplicate and the data were analysed to obtain mean mass/rate values and standard deviations.

Qualitative Analyses of CI-4 Volatiles

Analysis of gases in the air space above cultures of CI-4 grown for eight days at 23° C. on PDA were conducted according to the following protocol as described by Strobel (Strobel, et al., 2001, Microbiology 147:2943-2950). First, a baked "Solid Phase Micro Extraction" syringe (Supelco) consisting of 50/30 divinylbenzene/carboxen on polydimethylsiloxane on a Stable Flex fibre was placed through a small hole drilled in the side of the Petri plated and exposed to the vapour phase for only 5 min due to the high concentration of fungal VOCs. The syringe was then inserted into the splitless injection port of a Hewlett Packard 6890 gas chromatograph containing a 30 m×0.25 mm I.D. ZB Wax capillary column with a film thickness of 0.50 μm. The column was temperature programmed as follows: 30° C. for 2 min increased to 220° C. at 5° C. $min^{-1}$. The carrier gas was ultra high purity helium, and the initial column head pressure was 50 kPa. Prior to trapping the volatiles, the fiber was conditioned at 240° C. for 20 min under a flow of helium gas. A 30 sec injection time was used to introduce the sample fiber into the GC. The gas chromatograph was interfaced to a Hewlett Packard 5973 mass selective detector (mass spectrometer) operating at unit resolution. The MS was scanned at a rate of 2.5 scans per second over a mass range of 35-360 amu. Data acquisition and data processing were performed on the Hewlett Packard ChemStation software system. Tentative identification of the compounds produced by CI-4 was made via library comparison using the NIST database, and all chemical compounds described in this report use the NIST data base chemical terminology. Final confirmatory identification was made for any compounds with available authentic standards obtained from Sigma/Aldrich by comparing the GC/MS data of the standards, including 1-8-cineole and 1-methyl-1,4-cyclohexadiene, with GC/MS data of fungal products. The GC/MS tests were conducted several times under different exposure times of the fibre to fungal gases with the 5 min. exposure being the optimum given the large volume of VOCs being made by the fungus.

Quantification of Fungal Volatiles

PTR-MS was used to quantify production of fungal volatiles on a continuous monitoring basis beginning with a 2.5 day old culture growing on a 300 ml slant of PDA in a 1 L bottle at 20±2° C. The bottle possessed an O-ring sealed cap that had been modified to possess both inlet and outlet tubes with 10 std cc/min of purified compressed air (Ezra, et al., 2004, Plant Science 166:1471-1477)(FIG. 1). Monitoring of all ions in produced in the spectrum was done for 7.5 days and the concentration of VOCs was estimated (Ezra, et al., 2004, Plant Science 166:1471-1477; Bunge, et al., 2008, Appl Environ Microbiol 74: 2179-2186; Strobel, et al., 2008, Microbiology 154:3319-3328). Air-space analysis of the cultured and uninoculated samples was done by passing a small flow of air (medical-grade compressed air) through the culture bottles and then diluted with air of the same quality (FIG. 1). The sample lines were constructed entirely from PFA Teflon tubing and fittings. A ⅟₂₀-⅟₁₀ dilution kept the measurements within the linear dynamic range of the instrument and prevented water from condensing in the sample lines. Mass spectral scans were acquired from 20 to 220 Da.

It is to be recognized that the PTR-MS instrument ionizes organic molecules in the gas phase through their reaction with $H_3O^+$, forming mostly protonated molecules ($MH^+$, where M is the neutral organic molecule) which can then be detected by a standard quadrupole mass spectrometer. This process can be run on real air samples with or without dilution, since the primary constituents of air (nitrogen, oxygen, argon and carbon dioxide) have a proton affinity less than water and thus are not ionized. Most organic molecules (excepting alkanes) have a proton affinity greater than water and are therefore ionized and detected. A further advantage of PTR-MS is that from the known or calculated quantities, the reaction time, the amount of $H_3O^+$ present, and the theoretical reaction rate constant for the proton transfer reaction, the absolute concentration of constituents in a sample can be quantified (Lindinger, et al., 1998, Int J Mass Spectrum Ion Process 173:191-241). Finally, an enormous advantage of PTR-MS is that it can be run in real time and continuously produce data on the concentrations of specific ions of interest.

Concentrations derived from the PTR-MS measurements were calculated using equations derived from reaction kinetics and assume that a reaction rate coefficient to $2 \times 10^{-9}$ ml $s^{-1}$ is appropriate for all compounds (Lindinger, et al., 1998, Int J Mass Spectrum Ion Process 173:191-241; Ezra, et al., 2004, Plant Science 166:1471-1477). This method provides a simple means by which the measured ion intensity at any mass can be expressed as an equivalent concentration. In the event that a particular ion can be ascribed to a single compound, then the concentration of that specific compound can be determined using the same procedure as above followed by correction for dilution and any product ion fragmentation. The product ion distribution is determined from mixtures prepared from pure standards.

Biological Activities of the VOCs of *Hypoxylon* sp.

The degree of susceptibility of the assay test organisms was dependent upon the age of the *Hypoxylon* sp. culture to which they were exposed for 24 hr (Table 1).

TABLE 1

Progressive (time course) bioassay showing susceptibility of selected fungal pathogens to *Hypoxylon* sp. VOCs as a function of *Hypoxylon* sp. culture age with a 24 hr exposure to the fungal VOCs. The percentages reported are relative to growth of the test organism on a PDA plate minus *Hypoxylon* sp.

| Test Organism | 3 days | 4 days | 5 days | 6 days | 7 days |
|---|---|---|---|---|---|
| Phytophthora palmivora | −16.6% ± 7.8 | 11.1% ± 0.0 | 88.8% ± 0.0 | 100.0% ± 0.0 | 100.0% ± 0.0 |
| Geotrichium candidum | 12.5% ± 0.0 | 6.2% ± 8.8 | 25.0% ± 0.0 | 31.2% ± 8.8 | 25.0% ± 17.6 |
| Rhizoctonia solani | 75.0% ± 35.3 | 75.0% ± 35.3 | 37.5% ± 53.0 | 87.5% ± 17.6 | 100.0% ± 0.0 |
| Sclerotinia sclerotiorum | 28.5% ± 0.0 | 67.8% ± 15.1 | 100.0% ± 0.0 | 100.0% ± 0.0 | 100.0% ± 0.0 |
| Aspergillus fumigatus | 10.0% ± 14.1 | 40.0% ± 0.0 | 50.0% ± 14.1 | 100.0% ± 0.0 | 75.0% ± 35.3 |
| Pythium ultimum | −3.4% ± 4.9 | 43.0% ± 14.8 | 58.1% ± 6.5 | 97.6% ± 3.2 | 100.0% ± 0.0 |
| Fusarium solani | 31.2% ± 0.0 | 15.6% ± 4.4 | 31.2% ± 8.8 | 56.2% ± 17.6 | 43.7% ± 8.8 |
| Phytophthora cinnamomi | 6.2% ± 44.1 | 50.0% ± 35.3 | 75.0% ± 0.0 | 100.0% ± 0.0 | 100.0% ± 0.0 |
| Trichoderma viridae | 16.6% ± 16.8 | 4.7% ± 6.7 | 19.0% ± 6.73 | 23.8% ± 0.0 | 4.7% ± 0.0 |
| Cercospora beticola | 41.6% ± 11.7 | 50.0% ± 0.0 | 75.0% ± 35.36 | 100.0% ± 0.0 | 100.0% ± 0.0 |

A progressive (time course) assay using ten different fungal pathogens was designed to determine the time point at which maximum sensitivity of the test organisms occurred which may also relate to the maximum point of VOC production by the fungus Inhibitory activity of VOCs produced after three, four, five, six, and seven days was compared and maximum inhibition, suggesting the highest concentration of volatile bioactive substances, occurred at six days with eight of the ten test organisms exhibiting maximum inhibition at this time point. The most sensitive test organisms to the VOCs of *Hypoxylon* sp. were *Phytophthora* spp., *Sclerotinia sclerotiorum*, *Aspergillus fumigatus*, and *Cercospora beticola* (Table 1).

An expanded bioassay test involving 16 plant associated fungi revealed varying degrees of response when evaluated via a bioassay Petri plate test system (Strobel, et al., 2001, Microbiology 147:2943-2950). The organisms showed minimal to complete inhibition with a three day exposure to fungal VOCs from a six day old culture of *Hypoxylon* sp., while there was no inhibition of various yeasts and bacteria (Table 2).

TABLE 2

Effects of the VOCs of a 6 day old culture of *Hypoxylon* sp. on various fungi. Inhibition values were calculated as a percentage of growth inhibition as compared to an untreated control test organism at a 3 day exposure. Tests were conducted in triplicate and results varied as indicated by standard deviations. All organisms were viable after exposure to fungal VOCs.

| Test Organism | Percent Inhibition | D or A |
|---|---|---|
| *Sclerotinia sclerotiorum** | 90.4% ± 16.5 | A |
| *Fusarium solani* | 63.0% ± 5.6 | A |
| *Mycosphaerella fijiensis* | 50.0% ± 57.7 | A |
| *Pythium ultimum** | 78.2% ± 14.3 | A |
| *Verticillium dahliae* | 80.0% ± 34.6 | A |
| *Aspergillus fumigatus** | 43.0% ± 16.8 | A |
| *Phytophthora palmivora** | 70.0% ± 38.3 | A |
| *Ceratocystis ulmi* | 42.8% ± 32.0 | A |
| *Botrytis cinerea* | 100.0% ± 0.0 | A |
| *Colletotrichum lagenarium* | 36.1% ± 12.7 | A |
| *Geotrichium candidum** | 27.0% ± 6.7 | A |
| *Rhizoctonia solani** | 66.6% ± 57.7 | A |
| *Phytophthora cinnamomi** | 100.0% ± 0.0 | A |
| *Trichoderma viridae** | 50.0% ± 4.7 | A |
| *Cercospora* beticola* | 100.0% 0.0 | A |
| *Muscodor albus* | 58.3% ± 11.7 | A |

*Denotes organism was also used in the progressive bioassay test system.
D = Dead and A = Alive All organisms, including those exhibiting complete inhibition in the presence of fungal VOCs were viable upon re-culturing on PDA. The most sensitive fungi were *Phytophthora* spp., *Cercospora beticola*, *Sclerotinia sclerotiorum*, and *Botrytis cinerea* (Table 2).

Composition of Volatiles Produced by *Hypoxylon* sp.

Several GC/MS analyses were conducted on the VOCs produced by an eight day old culture of *Hypoxylon* sp. Controls consisting of uninoculated PDA Petri plates were used to subtract compounds contributed by the medium. Preliminary identification of fungal VOCs was determined by comparison of unknown volatiles with MS data of reference compounds listed in the NIST database. It is to be noted that the bulk of the VOCs could not be conclusively identified. However, for those VOCs which could be identified, authentic standards were used to confirm the identification of possible compounds and included 1,8-cineole and 1-methyl-1,4-cyclohexadiene. In addition, other compounds were tentatively identified on the basis of the % quality of the match to the NIST data base with an arbitrary cut off at 60% quality match. The most abundant compound, as based upon total integrated peak areas of the GC elution profile, was tentatively identified as (+)-α-methylene-α-fenchocamphorone, a monoterpene (Table 3) (FIG. 5).

TABLE 3

A GC/MS air-space analysis of the volatile compounds produced by *Hypoxylon* sp. after eight days incubation at 23° C. on PDA using a SPME fiber. Compounds present in a control PDA Petri plate have been subtracted from the data. Unknown compounds represent those with a quality % value less than 60.

| Retention Time (min) | Relative Area | Possible Compound | Mol. Mass (Da) | Quality |
|---|---|---|---|---|
| 4.53 | 7.3 | *1,4-Cyclohexadiene, 1-methyl- | 94 | 91 |
| 9.01 | 7.6 | *1,8-Cineole | 154 | 96 |
| 13.99 | 58.1 | Cyclohexane, 1,2,4-tris(methylene)-(or isomer) | 120 | 83 |
| 14.22 | 4.6 | 8-anti-methylbicyclo(3.2.1)octa-2,6-diene (or isomer) | 120 | 83 |
| 14.28 | 2.0 | 8-anti-methylbicyclo(3.2.1)octa-2,6-diene (or isomer) | 120 | 87 |
| 14.33 | 3.4 | 1,2,4-Tris(methylene)-cyclohexane (or isomer) | 120 | 81 |
| 21.89 | 1.4 | 6-Aza-1,2,3,3a-tetrahydropyrrolo[1,2-a]quinoxalin-4 | 189 | 83 |
| 23.13 | 2.5 | Unknown | 136 | |
| 25.21 | 5.9 | Unknown | 114 | |
| 26.11 | 2.3 | 5-ethyl-4,4,5-trimethyl-2-cyclopenten-1-one | 152 | 62 |
| 27.67 | 10.9 | Unknown | 110 | |
| 29.6 | 206.7 | ?(+)-α-methylene-α-fenchocamphorone | 150 | 62 |
| 29.71 | 111.5 | 7-Oxatetracyclo[4.1.0.0(2,4).0(3,5)]heptane | 94 | 76 |
| 29.76 | 35.5 | Unknown | 94 | |
| 29.79 | 47.8 | Unknown | 92 | |
| 29.95 | 9.5 | Unknown | 108 | |
| 30.2 | 5.5 | Unknown | 144 | |
| 30.35 | 4.0 | Unknown | 150 | |
| 30.42 | 4.4 | Unknown | 66 | |
| 30.55 | 7.2 | Unknown | 138 | |
| 30.7 | 1.3 | Unknown | 103 | |
| 30.72 | 2.5 | Unknown | 150 | |
| 30.77 | 1.9 | 1H-inden-1-one, 2,3,3a,4,7,7a-hexahydro-7a-methyl-, | 150 | 68 |
| 30.88 | 2.6 | 2,4,6-Trimethyl-1,3-benzenediamine | 150 | 72 |
| 30.97 | 3.6 | Unknown | 150 | |
| 31.07 | 4.9 | Unknown | 150 | |
| 31.3 | 55.3 | ?(+)-α-methylene-α-fenchocamphorone | 150 | 78 |
| 31.43 | 1.9 | Unknown | 150 | |
| 32.53 | 1.5 | Unknown | 236 | |

*Denotes that the retention time and MS spectrum closely matched or were identical to an authentic standard compound. Those compounds without a designated footnote have a mass spectrum that most closely matched the appropriate compound in the NIST database. The unknowns had a Quality ranking of less than 60%.
?Denotes that a question remain as to the actual identity of the compound listed, the correct elution time of the actual product remains uncertain-the peaks could represent isomers of (+)-α-methylene-α-fenchocamphorone.

Figure 6:
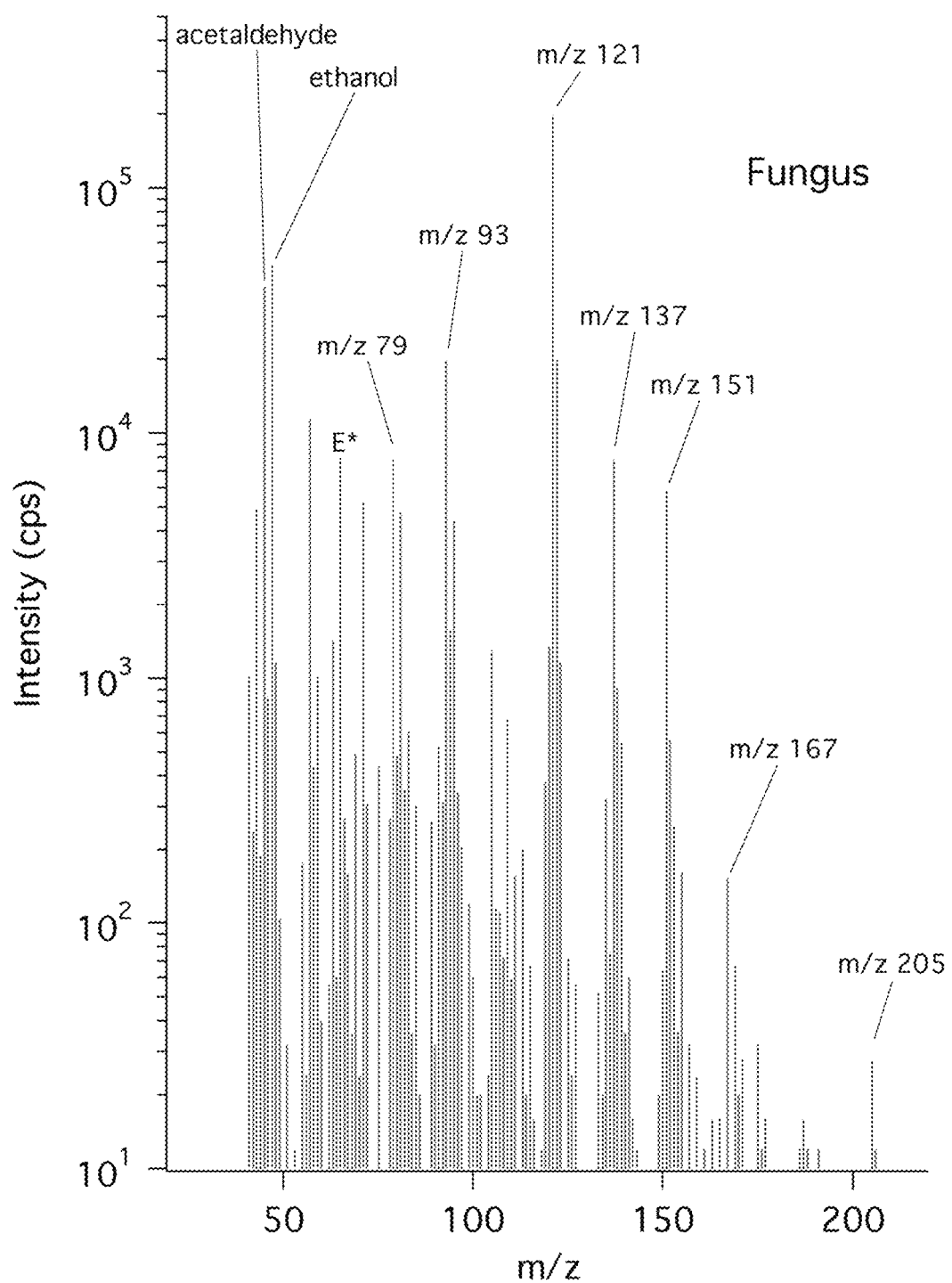
FIG. 6 is a PTR mass spectrum of the head space of a 5-day old culture of *Hypoxylon* sp.

However, at least two peaks appeared designated as this monoterpenoid and these have tentatively been assigned as isomers or relatives of fenchocamphorone since an authentic standard for this compound was not available. A second monoterpene detected in smaller quantities was identified as 1,8-cineole by its NIST data base match, its similarity to the authentic compound, the appearance of peaks at 81, 137 155 in the PTR mass spectrum (identical to its authentic standard), and its characteristic *eucalyptus* odor all of which are consistent with 1,8-cineole (Table 3; FIGS. 5, 6). The fungus also produced a third compound often considered a derivative of the monoterpene group, 1-methyl-1,4-cyclohexadiene (FIGS. 5, 6). Many other compounds appeared in the GC/MS analysis including cyclohexane, 1,2,4-tris(methylene)- (or isomer), and 8-anti-methylbicyclo(3.2.1)octa-2,6-diene (or isomer) which are probably the chief contributors in the PTR mass spectrum of the 121 peak (M plus H+) (Table 3) (FIG. 6). Other unidentified compounds, many in lesser amounts, were also seen in the VOCs of this fungus on each GC/MS analysis (Table 3). It is to be noted that the results of the GC/MS are at times inconsistent with the PTR-MS and this is due to the fact that the SPME fiber lacks universal adsorption efficiency and likewise the PTR-MS lacks the ability to discern protonated molecular species from other ion fragments. One of the notable discrepancies is the total lack, on repeated analyses, of the SPME fibre to trap the high amounts of ethanol and acetaldehyde that are present in the VOC mix as detected by PTR-MS (Table 3, FIGS. 6, 7). On the other hand, there are many examples in which the data sets of the two MS techniques are compatible, i.e. data for the compound with a MW of 120 and the 1,8 cineole spectra (Table 3 and FIG. 6).

The production of two, possibly three or more monoterpenes/monoterpene derivatives may suggest that the endophyte possesses the enzymatic machinery specialized for the biosynthesis of monoterpenic compounds that are usually associated with higher plants. Monoterpenes are naturally formed products generally associated as common constituents of essential oils and often contribute to antimicrobial activity (Madyastha, 1984, Journal of Chemical Sciences 93:677-686). Biosynthetic pathways leading to the production of such monoterpenes by *Hypoxylon* sp. may suggest possible insight as to its ability to grow in the presence of a highly biologically active fungus, *M. albus*. The comprehensive spectrum of antimicrobial activity exhibited by *M. albus* is yet to be matched by a VOC producing fungus (Strobel, et al., 2001, Microbiology 147:2943-2950). The ability to withstand its own monoterpenic antimicrobials may or may not be linked to its ability to withstand the potent volatile antimicrobials produced by *M. albus*.

Substrate Facilitation of VOC Production on Selected Media.

There were higher concentrations, in general, of volatile compounds, as detected by an olfactory method when *Hypoxylon* sp. was grown on media enriched with yeast extract over peptone as a source for amino acids (exception seen only in combination with starch). Media containing starch, glucose, and cellobiose as a source of carbohydrates, including PDA, oatmeal agar, and MP, also facilitated higher concentrations of detectable volatile compounds by olfactory methods.

Olfactory qualitative analyses were supported by quantitative measures of surface mycelial mat dry weight on each media type. Surface mycelial mass calculations were conducted following the qualitative analyses and yielded similar substrate preferences. While mass calculations seemed to be dependent first on amino acid sources and second on carbohydrate sources, olfactory ratings seemed to be most dependent on carbohydrate sources. The analyses were both run in duplicate and standard deviations were calculated (Table 4).

TABLE 4

Substrate facilitation of volatile production on different media showing qualitative olfactory observations based on independent ratings 1 to 5 (5 being optimum), and the dry weight of the surface mycelial mat.

| Media | Surface Mass (mg) | Olfactory Rating |
|---|---|---|
| (A.) Yeast | 2.5 ± 0.7 | 1.1 ± 0.4 |
| (B.) Peptone | 1.0 ± 0.0 | 1.3 ± 0.7 |
| (C.) Yeast + Cellulose | 1.5 ± 0.7 | 1.1 ± 0.4 |
| (D.) Peptone + Cellulose | 1.0 ± 0.0 | 1.0 ± 0.0 |
| (E.) Yeast + Starch | 26.5 ± 6.4 | 4.1 ± 1.3 |
| (F.) Peptone + Starch | 30.5 ± 3.5 | 4.1 ± 1.1 |
| (G.) Yeast + Glucose | 22.5 ± 0.7 | 4.0 ± 1.1 |
| (H.) Peptone + Glucose | 11.0 ± 4.2 | 3.4 ± 0.7 |
| (I.) Yeast + Cellobiose | 19.0 ± 1.4 | 3.1 ± 1.2 |
| (J.) Peptone + Cellobiose | 7.5 ± 0.7 | 2.8 ± 0.7 |
| (K.) Yeast + Glycerol | 3.5 ± 0.7 | 2.1 ± 1.2 |
| (L.) Peptone + Glycerol | 1.0 ± 0.0 | 1.5 ± 0.5 |
| (M.) MP | 50.0 ± 2.8 | 4.8 ± 0.5 |
| (N.) PDA | 33.0 ± 4.2 | 5.0 ± 0.0 |
| (O.) Oatmeal | 29.0 ± 2.8 | 5.0 ± 0.0 |

Quantification of the VOCs of *Hypoxylon* sp.

Figure 7:
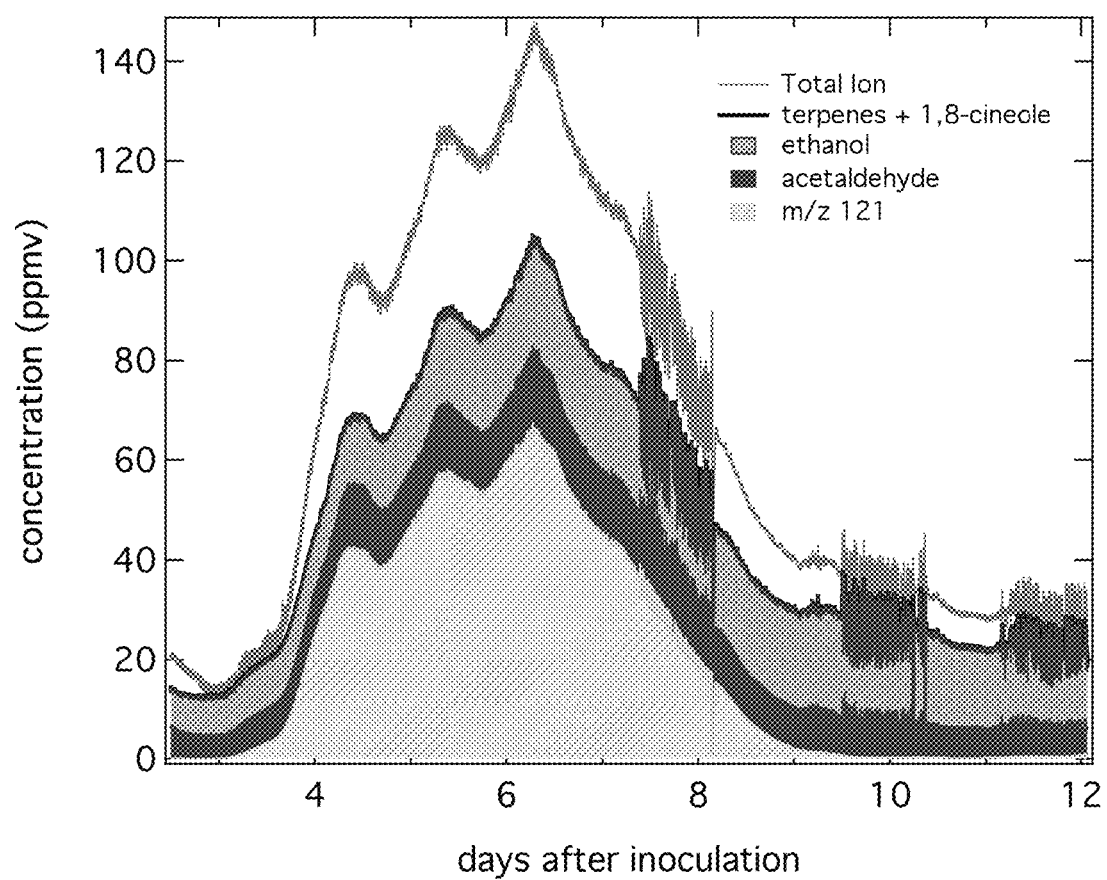
FIG. 7 is a graph of the production of individual compounds in the VOCs of *Hypoxylon* sp. as a function of time as measured and calculated from PTR mass spectral data. The m/z at 121 is likely the series of protonated cyclic alkanes/alkenes whose mass is 120 (See Table 3 herein). The terpenes including 1,8 cineole were calculated from contributions of compounds yielding masses 81, 137 and 155. All calculations are minus the PDA background control flask.

In order to quantify the concentration of volatile products being produced by *Hypoxylon* sp. continuously in the air space over in a 1 L bottle with a 300 ml slant of PDA, a direct method involving PTR-MS was used (FIG. 1). All ions in the PTR spectrum were monitored on a continuous basis and they ranged from mass 41-205 (FIG. 6). The maximum ion output was detected at ca. 6 days of incubation, which is consistent with the sensitivity of the assay organisms to the VOCs of *Hypoxylon* sp. (FIG. 7) (Table 1). Total maximum production of fungal VOCs was a 145 ppmv on day 6 and at a calculated rate of 7.65 ppmv/hr (FIG. 7). It seems that the overall VOC output of this fungus is substantial when compared to the output of other gas producing fungi (Ezra, et al., 2004a, Microbiology 150:4023-4031; Strobel, et al., 2008, Microbiology 154:3319-3328). The chief components of the gas mixture were compounds whose PTR mass spectra were consistent with ethanol, acetaldehyde, and a mass 121 which most likely represents protonated forms of unsaturated compounds whose mass is 120 (Table 3). Ions consistent with 1,8 cineole and other terpenoids producing masses at 81, 137 and 155 also allowed for an estimate of its concentration over the time course of the experiment and they peak at day 5.5-6 (FIG. 7). However, a direct estimate of 1,8 cineole production, based on mass 155, in the flask is ca. 800 ppbv at day 6 which is about 0.5% of the total fungal VOCs.

In summary, six day old cultures of *Hypoxylon* sp. displayed maximal VOC-antimicrobial activity against *Botrytis cinerea, Phytophthora cinnamomi, Cercospora beticola*, and *Sclerotinia sclerotiorum*, suggesting that the VOCs may play some role in the biology of the fungus and its survival in its host plant. Media containing starch- or sugar related substrates best supported VOC production by the fungus. Direct on-line quantification of VOCs was measured by proton transfer mass spectrometry (PTR-MS) covering a continuous range with optimum VOC production occurred at 6 days at 145 ppmv with a rate of production of 7.65 ppmv/hr. This demonstrates that 1,8-cineole (a monoterpene) is produced by a microorganism, which represents a novel and important source of this compound. This monoterpene is an octane derivative and has potential use as a fuel additive as do the other VOCs of this organism. Thus, fungal sourcing of this compound and other VOCs as produced by *Hypoxylon* sp. greatly expands their potential applications in medicine, industry, and energy production.

Example 2: Modulation of Volatile Organic Compound Formation in the Mycodiesel-Producing Endophyte *Hypoxylon* sp. CI-4

As described herein, an endophytic *Hypoxylon* sp. (strain CI-4) producing a wide spectrum of volatile organic compounds (VOCs), including 1,8-cineole, 1-methyl-1,4-cyclohexadiene and cyclohexane, 1,2,4-tris(methylene), was selected as a candidate for the modulation of VOC production. It was determined that production of these and other VOCs can be affected by using agents that may modulate the epigenetics of the fungus. Many of the VOCs made by this organism are of interest because of their high energy densities and thus the potential they might have as Mycodiesel fuels. Strain CI-4 was exposed to the epigenetic modulators suberoylanilide hydroxamic acid (SAHA, a histone deacetylase) and 5-azacytidine (AZA, a DNA methyltransferase inhibitor). After these treatments the organism displayed striking cultural changes, including variations in pigmentation, growth rates and odour, in addition to significant differences in the bioactivities of the VOCs.

The resulting variants were designated CI4-B, CI4-AZA and CI4-SAHA. GC/MS analyses of the VOCs produced by the variants showed considerable variation, with the emergence of several compounds not previously observed in the wild-type, particularly an array of tentatively identified terpenes such as a-thujene, sabinene, c-terpinene, a-terpinolene and b-selinene, in addition to several primary and secondary alkanes, alkenes, organic acids and derivatives of benzene. Proton transfer reaction mass spectroscopic analyses showed a marked increase in the ratio of ethanol (mass 47) to the total mass of all other ionizable VOCs, from ~0.6 in the untreated strain CI-4 to ~0.8 in CI-4 grown in the presence of AZA. Strain CI4-B was created by exposure of the fungus to 100 mM SAHA; upon removal of the epigenetic modulator from the culture medium, it did not revert to the wild-type phenotype. Without wishing to be bound to any particular theory, these results may have implications for understanding why there may be a wide range of VOCs found in various isolates of this fungus in nature.

The materials and methods employed in these experiments are now described.

Development of Epigenetic Variants

The wild-type *Hypoxylon* sp. had previously been found as an endophyte in *Persea indica* growing in the Laurisilva, Tenerife, Spain (Tomsheck et al., 2010, Microb Ecol 60:903-914). The fungus, growing on potato dextrose agar (PDA), was hyphal tipped in order to obtain a genetically pure strain, CI-4. This strain was used for epigenetic modulation using a histone deacetylase inhibitor, suberoylanilide hydroxamic acid (SAHA) and a DNA methyltransferase inhibitor, 5-azacytidine (AZA) as the modulating compounds (Cichewicz, 2010, Nat Prod Rep 27:11-22). Stock solutions of these compounds were prepared in DMSO and sterile deionized water, respectively. The fungus was grown on PDA supplemented with different concentrations of the epigenetic modulators (1, 5, 10, 20, 30, 50 and 100 µM) for 15 days. The numerous variants resulting from concentrations of modulators producing the most notable cultural, biological and VOC changes were selected for future study. The strains studied here were CI-4 (wild-type), CI4-B (strain selected after a 15 day exposure of CI-4 to 50 µM SAHA, hyphal tipped, transferred to PDA and studied without subsequent exposure to SAHA), CI4-SAHA (strain CI-4 exposed to 50 µM SAHA in all studies), and CI4-AZA (strain CI-4 exposed to 100 µM AZA in all studies).

Qualitative/Quantitative Analyses of Fungal VOCs
Weight Measurements of VOCs (Carbotrap Experiments)

In order to obtain quantitative weight measurements of the VOC production by the fungi, the fungi were grown for 14 days in 7 l potato dextrose (PD) broth, supplemented with 50 µM SAHA or 100 µM AZA as required, in 10 l flasks with shaking at 200 r.p.m. at 22° C., with an inflow of 800 ml sterile compressed air $min^{-1}$ through a 20 µm filter. The outlet was connected to a custom-designed stainless steel column containing Carbotrap materials (Supelco; Carbotraps A and B specifically for hydrocarbons) for adsorption of the hydrocarbon-like VOCs from each culture for quantitative and qualitative measurements.

The Carbotrap columns were eluted by heating in a programmable oven and purged with a flow of nitrogen gas as previously described (Booth et al., 2011, Biotechnol Lett 33:1963-1972) and weighed. Gravitometric analysis provided information on VOC yields. The efficiency of the column trapping method ranges from 65 to 70% according to Booth et al. (2011, Biotechnol Lett 33:1963-1972). In addition, the gas-trapping vial, having a septum, was gently warmed and thus directly prepared for qualitative GC/MS gas analysis.

GC/MS Analyses

Qualitative gas analysis of the compounds in the gas-trapping vials and regular Petri plate cultures was done on a preconditioned solid-phase micro-extraction (SPME) syringe (Supelco) consisting of 50/30 divinylbenzene/carboxen on polydimethylsiloxane on a Stable Flex fibre for 5 min (Booth et al., 2011, Biotechnol Lett 33:1963-1972). For Petri plate analysis (8-day-old cultures) it was placed through a small hole drilled in the side of the plate and exposed to the vapour phase for 30 min (Strobel et al., 2001, Microbiology 147:2943-2950). The syringe was then inserted into the splitless injection port of a Hewlett Packard 6890 gas chromatograph containing a 30 m×0.25 mm i.d. ZB Wax capillary column with a film thickness of 0.50 µm. The column was temperature programmed as follows: 30° C. for 2 min, increasing to 220° C. at 5° C. $min^{-1}$. The carrier gas was ultrahigh-purity helium, and the initial column head pressure was 50 kPa. A 30 s injection time was used to introduce the sample fibre into the chromatograph. The gas chromatograph was interfaced to a Hewlett Packard 5973 mass selective detector (mass spectrometer) operating at unit resolution. The spectra were acquired at a rate of 2.5 scans per second over a mass range of 35-360 amu. Data acquisition and data processing were performed on the Hewlett Packard ChemStation software system. Tentative identification of the fungal compounds was made via library comparison using the NIST database, and all chemical compounds described in this report use the NIST database chemical terminology. Only compounds with a quality match score better than 72% are listed and described in this report. All other unidentified compounds are lumped and summed for each strain tested. For some compounds, confirmatory identification was made with available authentic standards obtained from Sigma/Aldrich. This was done by comparing the GC/MS data of the standards, including 1,8-cineole, sabinene and others, with the GC/MS data of fungal products. The GC/MS tests were conducted several times with different exposure times of the fibre to fungal gases. Compounds appearing in the control flasks or plates were removed from the analysis and the data presented.

Proton-Transfer Mass Spectrometry (PTR-MS)

PTR-MS was used to quantify the production of fungal volatiles on a one-time monitoring basis on 10-day-old cultures growing in 10 l flask containing 7 l liquid medium as described above for the Carbotrap experiments. During the PTR-MS measurement, which lasted ~1 h, the sterile air flow through the culture flask was reduced from 800 to 50-100 ml min$^{-1}$. The outflow from the culture flask was disconnected from the Carbotraps and diluted with dry air at 500-1000 ml min$^{-1}$ before being directed to the inlet of the PTR-MS. This $\frac{1}{20}$-$\frac{1}{10}$ dilution kept the measurements within the linear dynamic range of the instrument and prevented water from condensing in the sample lines. The PTR-MS instrument was operated in the bar scan mode and mass spectral scans were obtained from 20 to 200 Da. These ion intensity measurements were converted to concentrations as previously described (Ezra et al., 2004b, Plant Sci 166:1471-1477; Bunge et al., 2008, Appl Environ Microbiol 74:2179-2186; Strobel et al., 2008, Microbiology 154: 3319-3328). The same analysis procedure was performed for both inoculated and uninoculated samples. At the end of the PTR-MS analysis the original flows were re-established and the outflow from the culture flasks was reconnected to the Carbotraps.

It should be recognized that the PTR-MS instrument ionizes organic molecules in the gas phase through their reaction with $H_3O^+$, forming mostly protonated molecules ($MH^+$, where M is the neutral organic molecule) which can then be detected by a standard quadrupole mass spectrometer (Lindinger et al., 1998, Int J Mass Spectrom Ion Process 173:191-241). This process can be run on real air samples with or without dilution, since the primary constituents of air (nitrogen, oxygen, argon and carbon dioxide) have a proton affinity less than water and thus are not ionized. Most organic molecules (except alkanes) have a proton affinity greater than water and are therefore ionized and detected. A further advantage of PTR-MS is that from the known or calculated quantities, the reaction time, the amount of $H_3O^+$ present and the theoretical reaction rate constant for the proton transfer reaction, the absolute concentration of constituents in a sample can be quantified (Lindinger et al., 1998, Int J Mass Spectrom Ion Process 173:191-241). Finally, an enormous advantage of PTR-MS is that it can be run in real time and continuously produce data on the concentrations of specific ions of interest.

Concentrations of molecules derived from the PTR-MS measurements were calculated using equations derived from reaction kinetics and assume that a reaction rate coefficient to $2\times10^{-9}$ ml s$^{-1}$ is appropriate for all compounds (Lindinger et al., 1998, Int J Mass Spectrom Ion Process 173:191-241; Ezra et al., 2004b, Plant Sci 166:1471-1477). This method provides a simple means by which the measured ion intensity at any mass can be expressed as an equivalent concentration. In particular, the ion whose mass is 47 (ethanol) was monitored along with the total concentration of all other ions appearing in the spectrum and the ratios were calculated. Computation of the ethanol concentration is complicated by the fragmentation of $MH^+$ through loss of $H_2O$, Since only the ethanol concentration was used to compare the samples on a relative basis, no attempt has been made to correct the reported concentrations for this loss of signal.

Bioactivities of CI-4 and its Epigenetic Variants

The VOCs produced by 7-day-old cultures of *Hypoxylon* sp. CI-4 and its variants were tested for inhibitory antimicrobial activity against selected pathogenic fungi according to a bioassay test system previously described for analysis of VOCs produced by *Muscodor albus* (Strobel et al., 2001, Microbiology 147:2943-2950). The time frame of 7-9-day-old cultures is optimal for VOC production. The assays were conducted by growing the test organism in one well (PDA or PDA plus an epigenetic modulator) of a quadrant plate and placing 3 mm plugs of test fungi in each of the remaining wells (always PDA). The plate was then wrapped with a single piece of Parafilm and incubated at 23° C. Growth of the filamentous test fungi was quantitatively assessed by making multiple measurements of growth extending from the edge of the inoculum plugs after 2-5 days and comparing them to those of corresponding controls as described previously (Strobel et al., 2001, Microbiology 147:2943-2950). The tests were performed multiple times and the standard deviation calculated for each test organism (Strobel et al., 2001, Microbiology 147:2943-2950).

The results of the experiments are now described.

Epigenetic Variants

Successful attempts were made to acquire a response of *Hypoxylon* sp. CI-4 to varying concentrations (1-100 μM) of epigenetic modifying agents. Growth of strain CI-4 on PD broth with 50 μM SAHA or 100 μM AZA produced the most striking changes in the morphology and bioactivities of the cultures; lower concentrations were seemingly ineffective. Independently, after culturing in the presence of these agents two variants, CI4-SAHA and CI4-AZA, were produced that had altered cultural characteristics (Table 5). In order for them consistently to behave in the same manner, they were always grown on medium supplemented with the particular concentration of the specific modulator. On transferring these variants to normal PDA plates, one isolate, modified with SAHA, displayed morphological characteristics and bioactivity different from both the wild-type and the SAHA-treated strain growing on the supplemented medium. This strain was designated CI4-B. However, when the strain growing with AZA was cultured in normal PD medium, it regained the characteristic odour, cultural characteristics and bioactivity of the wild-type. Thus, for this study, CI-4 (wild-type) and epigenetic variants CI4-SAHA and CI4-AZA were used. CI4-B (selected from the 50 μM SAHA culture) was also included since it maintained some characteristics of the CI4-SAHA culture (Table 5). Interestingly, the growth rate of CI4-B exceeded that of the other strains, including the wild-type CI-4 (Table 5). This was also true for the total production of weighable VOCs as acquired in the Carbotrap experiments (Table 5). The coloration of each of the organisms was different especially on the reverse side of the plate, with CI4-SAHA having the greatest amount of pigmentation and CI4-AZA having the least (Table 5).

TABLE 5

Characteristics of the epigenetic variants of *Hypoxylon* sp. as compared to the CI-4 wild-type strain

| Characteristic | CI-4 | CI4-SAHA | CI4-B | CI4-AZA |
| --- | --- | --- | --- | --- |
| Percentage of lateral growth on PDA as compared to CI-4 over 7 days | — | 94.4 ± 1.96 | 106.7 ± 1.44 | 49.0 ± 1.91 |

TABLE 5-continued

Characteristics of the epigenetic variants of *Hypoxylon* sp. as compared to the CI-4 wild-type strain

| Characteristic | CI-4 | CI4-SAHA | CI4-B | CI4-AZA |
|---|---|---|---|---|
| Dry cell weight in PD broth (total 6.51) after 2 weeks | 27.9 ± 3.7 | 27.1 ± 2.2 | 28.7 ± 1.7 | 35.8 ± 1.4 |
| Total quantity extracted via Carbotrap after 2 weeks (mg) | 37.4 ± 2.0 | 33.7 ± 2.4 | 58.3 ± 3.5 | 45.3 ± 2.7 |
| Growth on PDA | Covers whole plate in 15 days | Similar to CI-4 | Paste then CI-4 covers the plate in 13-14 days | Slower then CI-4, taking 20 days to cover the plate |
| Growth density | Dense, fuzzy | Dense, fuzzy | Dense, fuzzy | Thin and sparse |
| Pigmentation | Olive green to brownish mycelial pigmentation, varying to light brown towards the margins | Heavier mycelial pigmentation spreading from the centre towards the margin | Only one-third of the culture gets the light brown mycelial pigmentation; rest remains creamy | The characteristic pigmentation of the wild-type is absent, or very thin in the centre |
| Reverse side characteristics | Discontinuous dark brown colour halfway from the centre and lighter colour towards the margin | Heavy olive green to brownish pigmentation up to three-quarters of the diameter of the plate | Very thin pigmentation in the centre only | Creamy, lacking the olive to dark brown colour of the wild-type |

The results presented are a compilation of data from at least three cultures of each organism.
Numerical values are means ± sd.

Bioactivity of the Fungi

Bioactivity tests done on the VOCs of each organism indicated several important features among these variants (Table 6). The bioactivity of the VOCs differed in specificity as well as the extent of the inhibition of some of the test organisms (Table 6).

TABLE 6

Bioactivity of the VOCs of 7-day-old cultures of *Hypoxylon* sp. CI-4 and its epigenetic variants against a panel of test organisms on PDA

| Test organism | Inhibition (%)* | | | |
|---|---|---|---|---|
| | CI-4 | CI4-SAHA | CI4-B | CI4-AZA |
| *Aspergillus fumigatus* | 54.4 ± 3.0 | 63.8 ± 1.7 | 43.7 ± 1.5 | 65.7 ± 2.6 |
| *Botrytis cinerea* | 52.0 ± 4.0 | 73.3 ± 2.3 | 70.8 ± 3.4 | 100 ± 0.0 |
| *Ceratocytis ulmi* | 100 ± 0.0 | 100 ± 0.0 | 100 ± 0.0 | 100 ± 0.0 |
| *Cercospora beticola* | 100 ± 0.0 | 100 ± 0.0 | 100 ± 0.0 | 100 ± 0.0 |
| *Colletotrichum lagenarium* | 46.2 ± 7.7 | 100 ± 0.0 | 25.7 ± 2.1 | 26.8 ± 0.0 |
| *Fusarium solani* | 71.9 ± 3.1 | 58.4 ± 3.8 | 10.5 ± 1.5 | 64.8 ± 3.2 |
| *Geotrichium candidum* | 61.90 ± 2.1 | 39.2 ± 3.4 | 25.0 ± 3.8 | 47.1 ± 0.0 |
| *Mucodor albus* | 16.7 ± 0.0 | 100 ± 0.0 | 22.2 ± 3.3 | 100 ± 0.0 |
| *Phytophthora palmivora* | 100 ± 0.0 | 100 ± 0.0 | 100 ± 0.0 | 100 ± 0.0 |
| *Phytophthora cinnamomi* | 100 ± 0.0 | 100 ± 0.0 | 100 ± 0.0 | 100 ± 0.0 |
| *Pythium ultimum* | 100 ± 0.0 | 100 ± 0.0 | 100 ± 0.0 | 100 ± 0.0 |
| *Rhizoctonia solani* | 100 ± 0.0 | 100 ± 0.0 | 100 ± 0.0 | 100 ± 0.0 |
| *Sclerotinia sclerotiorum* | 100 ± 0.0 | 44.9 ± 1.5 | 82.3 ± 1.6 | 100 ± 0.0 |
| *Trichoderma viride* | 21.9 ± 0.0 | 38.1 ± 1.6 | 19.2 ± 2.2 | 85.1 ± 1.6 |
| *Verticillum dahlia* | 100 ± 0.0 | 100 ± 0.0 | 100 ± 0.0 | 100 ± 0.0 |

*Relative to a control culture grown on PDA, Data are means ± SD.

The VOCs of all four strains inhibited *Ceratocystis ulmi*, *Cercospora beticola*, *Phytophthora palmivora*, *Phytophthora cinnamomi*, *Pythium ultimum*, *Rhizoctonia solani* and *Verticillum dahliae* completely. However, significant differences were found in the inhibition patterns of other test organisms. For instance, CI4-SAHA displayed 100% inhibition against *Colletotrichum lagenarium* and *Muscodor albus* as compared to 46.2% and 16.7% inhibition exhibited by CI-4 to these same organisms, respectively (Table 6). However, the effect on *Sclerotinia sclerotiorum* was reversed, as CI4-SAHA produced an inhibition of 44.9% compared to the complete inhibition by the wild-type CI-4 (Table 6). The epigenetic variant CI4-AZA inhibited *Botrytis cinerea* and *M. albus* completely while the wild-type showed only 52% and 16.7% inhibition, respectively. CI4-B showed an overall lower bioactivity than CI4-SAHA (Table 6). Overall, the results show that the epigenetic modulators are having an influence upon the VOC production by this fungus and further analytical chemical studies seemed warranted.

VOC Profiles of *Hypoxylon* sp. CI-4 and its Epigenetic Variants on PDA

GC/MS analysis of 8-day-old cultures of the fungi grown on PDA revealed significant variations in the VOCs, with several new compounds appearing in the epigenetic variants and several others not produced by comparison to the CI-4 wild-type (Table 7).

TABLE 7

Comparison of VOCs in *Hypoxylon* sp. CI-4 and its epigenetic variants by the SPME fibre analytical technique on 8-day-old cultures on PDA plates

| Wild-type CI-4 | CI4-SAHA | CI4-B | CI4-AZA |
|---|---|---|---|
| Ethyl alcohol | Ethyl alcohol | Ethyl alcohol | Ethyl alcohol |
| 1,4-Cyclohexadiene, 1-methyl- | 1,4-Cyclohexadiene, 1-methyl- 1,3,5-Cyclooctatriene | 1,4-Cyclohexadiene, 1-methyl- | 1,4-Cyclohexadiene, 1-methyl- 1,3,5-Cyclooctatriene |
| 1,8-Cineole | 1,8-Cineole | 1,8-Cineole Bicyclo [4.2.0] octa-1,3,5-triene Spiro [4.4] nona-1,6-dine, (5)- | 1,8-Cineole Benzene, 1-ethyl-3-methyl- |
| Benzene, 1-ethyl-3-methyl- 2,3-Heptadien-5-yne, 2,4-dimethyl- | 2,3-Heptadien-5-yne, 2,4-dimethyl- | 2,3-Heptadien-5-yne, 2,4-dimethyl- | 2,3-Heptadien-5-yne, 2,4-dimethyl- |
| Cyclohexane, 1,2,4-tris(methylene)- | Cyclohexane, 1,2,4-tris(methylene)- | Cyclohexane, 1,2,4-tris(methylene)- 1,4-Cyclooctadiene, 6-bromo- | Cyclohexane, 1,2,4-tris(methylene)- |
| Naphthalene, 1,2,4a,5,8,8a-hexahydro-4,7-dimethyl-1-(1-methylethyl)-, [1s-(1α,4aβ,8aα)]- |  |  | Naphthalene, 1,2,4a,5,8,8a-hexahydro-4,7-dimethyl-1-(1-methylethyl)-, [1s-(1α,4aβ,8aα)] |
| Phenylethyl alcohol |  | Phenylethyl alcohol | Phenylethyl alcohol (−)-Aristolene 1,5-Cyclooctadiene, 3-bromo- |
| 6a-Methyl-hexahydropentalene-1,6 |  |  | 6a-Methyl-hexahydropentalene-1,6 |
|  | 2,5-Methano-1H-inden-7(4H)-one, hexahydro-3a,7a-dimethyl- |  | 2,5-Methano-1H-inden-7(4H)-one, hexahydro-3a,7a-dimethyl- |
| 2-Naphtholenol, 3-methoxy | 2-Naphtholenol, 3-methoxy | 2-Naphtholenol, 3-methoxy | 2-Naphtholenol, 3-methoxy |

Most notably, (−)-aristolene and 1,5-cyclooctadiene, 3-bromo- were detected in CI4-AZA plus most of the other compounds associated with CI-4 (Table 7). In the VOCs of CI4-SAHA and CI4-B, benzene, 1-ethyl-3-methyl-, and naphthalene, 1,2,4a,5,8,8a-hexahydro-4,7-dimethyl-1-(1-methylethyl)-, [1s-(1α,4aβ,8aα)]- were absent (Table 7). These compounds were present in the VOCs of CI-4. In addition to these changes, uniquely, CI4-B also produced bicyclo[4.2.0]octa-1,3,5-triene along with spiro[4.4] nona-1,6-diene, (S)- and 1,4-cyclooctadiene, 6-bromo- (Table 7). Some of these compounds are of major interest because of their potential as fuels. Other compounds with fuel potential include ethyl alcohol, 1,4-cyclohexadiene-1-methyl- and cyclohexane, 1,2,4-tris(methylene)-, plus 1,8-cineole, which were detected in the VOCs of each variant (Table 7). The unknowns associated with the VOCs in these organisms are not shown. As surmised, the variations in VOC composition of these cultures offer some explanation as to the variation in bioactivity of the volatiles observed against different test organisms (Table 6), but the exact explanation for the variation is unknown.

VOC Profiles of *Hypoxylon* sp. CI-4 and its Epigenetic Variants on PD Broth

Commonly, fungi behave in a different biochemical manner when grown in liquid shaken culture versus solid stationary culture. For this reason each of the organisms was grown in 7 l of its respective PD medium, with shaking for 14 days. Compounds with hydrocarbon-like characteristics were trapped on Carbotraps and the eluents weighed and analysed by GC/MS. The weights of the samples varied over the range 33-55 mg (Table 5). It is also noteworthy that the technique of trapping larger amounts (tens of milligrams) of the fungal VOCs and subsequent analysis by SPME-GC/MS yielded much cleaner GC separation results and thus better mass spectral analyses of the fungal products (Booth et al., 2011, Biotechnol Lett 33:1963-1972).

As expected, in the fungi treated with chemical modulators, new compounds appeared, and the production of other compounds was lost. For instance, as was the case with the solid culture, sesquiterpenoids also appeared in the CI4-AZA liquid culture (m/z 204) and they had not been previously observed in the wild-type culture (Tables 7 and 8). Likewise, numerous terpenoids also appeared in the epigenetically modulated fungi, with the greatest number of them in CI4-AZA (m/z 204) (Table 8). The monoterpenoid γ-terpinene appeared in each of the modulated fungi but not the wild-type (Table 8). On the other hand, 1,8-cineole and cyclohexane, 1,2,4-tris(methylene), well-established volatile products of CI-4, were also detected in each variant (Table 8). Finally, many VOCs found in the wild-type fungus did not appear in the variants, including cyclohexene, 1 (1-propynyl)-; undecane, 5-methyl-; 2,4,5-trimethyl-1,3-dioxolane; and o-cymene (Table 8).

TABLE 8

Comparison of VOC production of *Hypoxylon* sp. CI-4 and its epigenetic variants, collected and eluted from Carbotraps and subsequently analysed by SPME-GC/MS

| | | | Relative area (%) | | | | |
|---|---|---|---|---|---|---|---|
| RT (min) | Compound | m/z | CI-4 | C14-SAHA | C14-B | C14-AZA | Quality match (%) |
| 1.85 | Acetaldehyde* | 44 | 2.40 | 1.31 | 2.01 | 0.93 | 74, 83, 74, 74 |
| 5.22 | 2,4,5-Trimethyl-1,3-dioxolane | 116 | 0.74 | | | | 87 |
| 5.24 | Decane* | 142 | | | | 1.22 | 95 |
| 6.15 | Undecane, 5-methyl-* | 170 | 0.21 | | | | 81 |
| 6.16 | α-Thujene | 136 | | 9.61 | 13.18 | 2.63 | 94, 94, 94 |
| 6.70 | 2-Butenal* | 70 | 0.47 | 1.37 | 0.92 | 1.40 | 91, 91, 91, 91 |

TABLE 8-continued

Comparison of VOC production of *Hypoxylon* sp. CI-4 and its epigenetic variants, collected and eluted from Carbotraps and subsequently analysed by SPME-GC/MS

| RT (min) | Compound | m/z | CI-4 | C14-SAHA | CI4-B | CI4-AZA | Quality match (%) |
|---|---|---|---|---|---|---|---|
| 7.70 | Decane, 3,6-dimethyl- | 170 | 0.20 | | | | 83 |
| 7.96 | 1,3,5-Trioxane, 2,4,6-trimethyl- | 132 | 0.58 | | | | 87 |
| 8.03 | Dodecane* | 170 | | | | 1.86 | 80 |
| 8.55 | Sabinene* | 136 | | | 0.36 | | 81 |
| 8.72 | 1-Butanol, 3-methyl, acetate* | 130 | 0.40 | 0.31 | | | 90, 72 |
| 8.83 | 1,3-Cyclopentadiene, 5-(1-methylpropylidene)- | 120 | 0.21 | | | | 72 |
| 9.15 | Cyclohexene, 1(1-propynyl)- | 120 | 0.23 | | | | 87 |
| 9.82 | β-Myrcene | 136 | | | 1.86 | 4.75 | 94, 94 |
| 9.93 | 2-Butenoic acid, ethyl ester (E) | 114 | | 0.37 | | | 86 |
| 11.67 | 4-Octanone* | 128 | 0.55 | 0.59 | | | 90, 90 |
| 11.85 | 1,8-Cineole* | 154 | 33.39 | 36.77 | 25.03 | 3.39 | 93, 97, 93, 96 |
| 12.17 | 1,3,6-Octatriene, 3,7-dimethyl-(trans-ocimene) | 136 | | | 0.75 | 0.82 | 95, 95 |
| 12.26 | 2-Butenoic acid, 2-methyl, ethyl ester | 128 | | 0.53 | | | 93 |
| 12.30 | Benzene, 1-ethenyl-2-methyl- | 118 | 0.19 | | | 0.83 | 76, 94 |
| 12.41 | γ-Terpinene* | 136 | | 0.31 | 3.43 | 1.84 | 97, 96, 96 |
| 12.55 | 1,3,7-Octatriene, 3,7-dimethyl- | 136 | | | 0.57 | | 95 |
| 12.99 | Benzene, 1,2,3,4-tetramethyl- | 134 | | | | 16.39 | 76 |
| 13.1 | Benzene, 1-methyl-4-(1-methylethyl)-(o-cymene) | 134 | 32.61 | | | | 94 |
| 13.18 | Benzene, 1-methyl-2-(1-methylethyl)-* | 134 | | 30.46 | 20.81 | | 95, 95 |
| 14.22 | Cyclohexane, 1,2,4-tris(methylethyl)-* | 120 | 6.73 | 1.19 | 2.43 | 10.35 | 95, 95, 95, 97 |
| 13.39 | α-Terpinolene* | 136 | | | 1.11 | 0.52 | 98, 98 |
| 16.69 | Benzene, 2-propenyl- | 118 | | | 0.47 | | 95 |
| 17.14 | 1-β-Pinene | 136 | 0.88 | | | | 91 |
| 19.26 | 1-Phellandene | 136 | 0.75 | | | | 72 |
| 20.03 | Linalool | 154 | | | | 0.36 | 95 |
| 20.18 | 2-β-Pinene | 136 | | 2.38 | | | 70 |
| 20.62 | cis-p-2-Menthen-1-ol | 154 | | 0.48 | | | 93 |
| 21.05 | α-Guaiene | 204 | | | | 0.50 | 99 |
| 21.60 | 3-Cyclohexene-1-ol, 4-methyl-1-(1-methylethyl)- | 154 | 0.27 | 0.48 | 0.46 | 3.18 | 97, 97, 97, 97 |
| 21.89 | 2-(2-Propenyl)-furan | 108 | | | | 0.96 | 70 |
| 22.02 | 4-(Cyclopentylidene)-2-butanone | 138 | | | | 1.27 | 72 |
| 23.78 | 1α-Terpineol | 154 | | | | 15.15 | 91 |
| 23.83 | Linalyl propionate | 210 | 0.90 | 1.57 | 2.12 | | 91, 91, 91 |
| 24.02 | β-Selinene | 204 | | | | 5.92 | 83 |
| 24.11 | δ-Guaiene | 204 | | | | 0.65 | 99 |
| 24.47 | Camphene | 136 | | | | 0.45 | 74 |
| 24.77 | Cyclopentane, 1-methylene-3-(1-methylethylidene) | 122 | | | | 2.02 | 72 |
| | Unknowns | | 18.09 | 12.27 | 24.47 | 22 | |

The fungi were grown with shaking in 7 1PD broth (10 1 flasks) for 2 weeks at 23° C., RT, retention time.
*Compounds whose retention times and mass spectra were close or identical to authentic standards.

Of interest was the appearance of several alkanes in the GC/MS analysis of the modulated fungi, including decane and dodecane, as well as several benzene derivatives including benzene, 1,2,3,4-tetramethyl- along with benzene, 2-propenyl- and o-cymene (Table 8). Other differences in VOC products were observed in the variants versus the wild-type fungus (Table 8).

Thus the epigenetic modification produced a range of outcomes: (1) the loss of the production of certain VOCs, (2) the appearance of new VOCs, and (3) no effect on the production of some VOCs (Tables 7 and 8).

Quantification of VOCs

Figure 8:
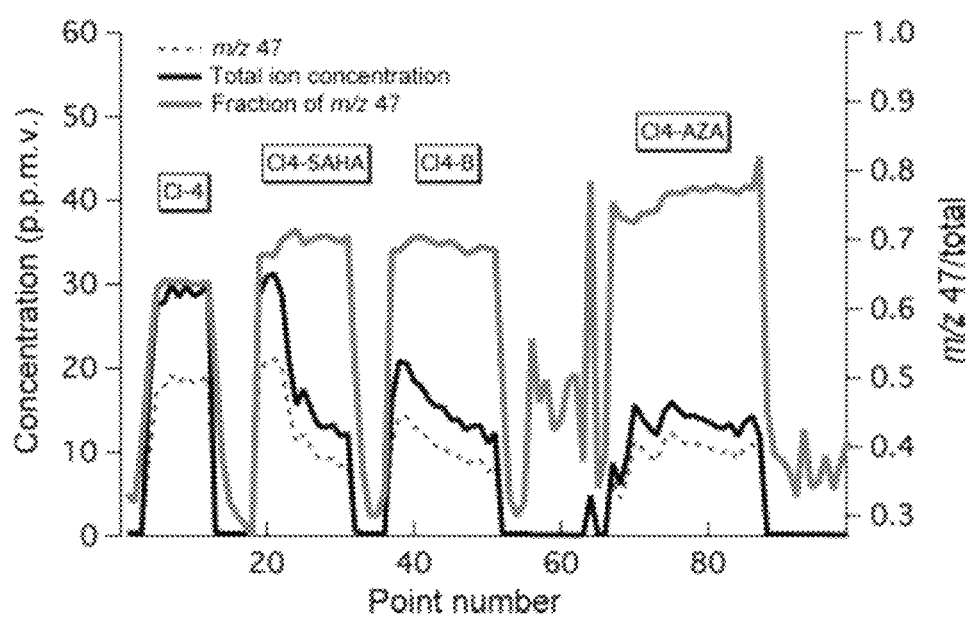
FIG. 8 is a graph of the gas production by *Hypoxylon* sp. cultures that were grown in 7 l PD broth and were 10 days old at the time of monitoring of the VOCs of the culture by PTR/MS. The left axis represents the total ion concentration and the right axis represents the ratio of mass 47 (ethanol) to the total ion concentration. The PTR/MS traces of each fungal culture are labelled with the respective fungal culture designation.

Using PTR-MS analysis it was possible to do direct on-line monitoring of the VOC production of each 7 l fungal culture. Monitoring was done at day 10 of the culture for 1 h with constant shaking. The total ion concentration of each of the epigenetic variants was reduced as compared to the control wild-type fungus (FIG. 8). However, the qualitative PTR-MS spectra obtained from each organism were all virtually identical (data not shown). This result seems at odds with conclusions drawn from the SPME-GC/MS analyses of Carbotrapped and concentrated VOCs in that, whereas striking differences in the VOCs were detected by that technique (Table 8), the amounts of most products were not great enough to be detectable by PTR-MS, which was conducted on the gas phase during the culture cycle. However, monitoring of the m/z at 47 (ethanol) along with the total ion concentration of VOC products showed that considerably less ethanol was produced by the variants, especially CI4-B and CI4-AZA. The most striking result from PTR-MS was the marked increase in the ratio of mass 47 (ethanol) to the total ion concentration in the variants: in the wild-type the ratio was about 0.65 but it increased to nearly 0.8 in the CI4-AZA culture (FIG. 8). It should be noted that ethanol was not recovered from the Carbotrap column since it was too polar for the column materials used and thus passed through the column.

Epigenetic Modulation and VOCs

VOCs not previously observed as products of CI-4 appeared after exposure to the epigenetic modulators SAHA or AZA (Tables 7 and 8). The majority of newly appearing products was mono- and sesquiterpenoids (Table 8). Furthermore, the new products arising in the epigenetic variants, especially the monoterpenoids, have potential as fuels, as exemplified by γ-terpinene, various benzene derivatives and 1,3,7-octratriene, 3,7-dimethyl-.

It is interesting that the epigenetic modulating compound SAHA generally caused a reversed effect on the overall biological properties of the wild-type fungus. That is, once the fungus was removed from a culture medium containing SAHA it generally reverted to an organism having the same cultural characteristics as the wild-type. However, in one case, a hyphal tip from a SAHA culture developed into an organism, CI4-B, having a set of phenotypic characteristics including coloration, colony type, bioactivity and VOC production that were unique to it, and these characteristics were maintained even without the presence of SAHA (Tables 5-8). Thus, it seems that simple chemical epigenetic methods can result in stable mutants having unique phenotypic characteristics. As expected, the variant CI4-B did have some characteristics of CI4-SAHA, including its ability to make benzene, 1-methyl-2-(1-methylethyl)-, and its PTR mass spectrum was nearly identical to that of CI4-SAHA with respect to ethanol production and the ratio of ethanol to the total ion concentration (Table 8, FIG. 8). Without wishing to be bound to any particular theory, this suggests that the CI4-B was not a random mutant and that the influence of SAHA on the fungus resulted in one or more permanent epigenetic modifications.

These results also demonstrate that *Hypoxylon* sp. CI-4 has the genetic potential to produce a wide spectrum of hydrocarbon-related molecules (Mycodiesel), and collectively these should be examined as potential fuels or other resource materials. Regular diesel fuel, from many locations, has a number of major families of molecules represented in it, including straight-chained and branched hydrocarbons, cyclohexanes, benzenes and naphthene-like molecules. The VOCs made by *Hypoxylon* sp. CI-4 and its epigenetic variants include representative molecules within these major families. This is exemplified by straight-chained and branched hydrocarbons (decane, dodecane, undecane, 5-methyl- and decane, 3,6-dimethyl-), cyclohexanes [cyclohexane, 1,2,4-tris(methylene); cyclohexene, 1(1-propynyl)-] benzyl derivatives [benzene, 1-ethenyl-2-methyl-, benzene, 1,2,3,4-tetramethyl-, benzene, 1-methyl-4-(1-methylethyl)-, benzene, 1-methyl-2-(1-methylethyl)- and benzene, 2-propenyl-] and naphthene derivatives [naphthalene, 1,2,4a,5,8,8a-hexahydro-4,7-dimethyl-1-(1-methylethyl)-, [1s-(1α, 4aβ,8aα)]-] (Tables 7 and 8). Other useful fuel molecules are also produced by these organisms, including ethanol and 1,8-cineole (an octane derivative) (Table 8, FIG. 8). Epigenetic modification experiments, such as these, provide a basis for a wider understanding of the genetic potential of an organism.

Without wishing to be bound by any particular theory, an extrapolation of the observations in this study to other fungi and biological situations implies that the genetic potential of any fungus is much greater than one may guess on first inspection. Furthermore, the phenomenon of epigenetics may help explain the observations that the VOC compositions of no two endophytic *Hypoxylon* isolates are ever the same. While many make the standard VOCs such as 1,8-cineole and cyclohexane, 1,2,4-tris(methylene), other products also appear that no two organisms hold in common. Without wishing to be bound by any particular theory, it may be that epigenetic modulation of a fungus can occur via mechanisms associated with its respective host plant, which may have broad implications in pathology and industrial microbiology.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed:

1. A method for generating mutant strains of a fungus with an increased production rate or production amount of at least one compound selected from the group consisting of 1,8-cineole, 1-methyl-1, 4-cyclohexadiene, and (+)-α-methylene-α-fenchocamphorone, comprising:
    mutating spores of the fungus;
    culturing the mutated spores; and
    screening the cultures of mutated spores for enhanced production rate or production amount of at least one compound selected from the group consisting of 1,8-cineole, 1-methyl-1, 4-cyclohexadiene, and (+)-α-methylene-α-fenchocamphorone.

2. The method of claim 1, wherein the fungus is from the genus *Nodulisporium*.

3. The method of claim 1, wherein the fungus is from the genus *Daldinia*.

4. The method of claim 1, wherein the fungus is from the genus *Hypoxylon*.

5. The method of claim 1, wherein the fungus has the imperfect stage of *Nodulisporium*.

6. The method of claim 1, wherein the fungus is an isolate selected from the group consisting of Co27-5 (deposited as NRRL 50500), C14A (deposited as NRRL 50501), Ti-13 (deposited as NRRL 50502), and Ec-38 (deposited as NRRL 50503).

7. The method of claim 1, wherein mutating the fungus comprises contacting the fungus with a chemical modulator.

8. The method of claim 7, wherein the chemical modulator is suberoylanilide hydroxamic acid (SAHA).

9. The method of claim 7, wherein the chemical modulator is 5-azacytidine (AZA).

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Chemically synthesized

<400> SEQUENCE: 1
tccgtaggtg aacctgcgg                                              19

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized

<400> SEQUENCE: 2
tcctccgctt attgatatgc                                             20